US012721967B2

(12) United States Patent
Guo et al.

(10) Patent No.: US 12,721,967 B2
(45) Date of Patent: Sep. 1, 2026

(54) SYSTEMS, DEVICES AND METHODS FOR DISPENSING FLOWABLE HEMOSTATS THAT INCORPORATE SAFETY MECHANISMS FOR PREVENTING AIR EMBOLISMS

(71) Applicant: Ethicon, Inc., Somerville, NJ (US)

(72) Inventors: Xuelin Guo, Livingston, NJ (US); Joseph LoRicco, Hillsborough, NJ (US); Gabriella Saade, West Windsor, NJ (US); Matthew Chan, West Chester, PA (US)

(73) Assignee: Ethicon, Inc., Raritan, NJ (US)

( * ) Notice: Subject to any disclaimer, the term of this patent is extended or adjusted under 35 U.S.C. 154(b) by 1205 days.

(21) Appl. No.: 17/695,958

(22) Filed: Mar. 16, 2022

(65) Prior Publication Data

US 2022/0313948 A1 Oct. 6, 2022

Related U.S. Application Data

(60) Provisional application No. 63/168,614, filed on Mar. 31, 2021.

(51) Int. Cl.
*A61M 25/00* (2006.01)
*A61L 26/00* (2006.01)
(Continued)

(52) U.S. Cl.
CPC ..... *A61M 25/0043* (2013.01); *A61L 26/0038* (2013.01); *A61M 5/3129* (2013.01);
(Continued)

(58) Field of Classification Search
CPC .......... A61M 2039/1083; A61M 39/10; A61M 2039/244; A61M 2039/0666;
(Continued)

(56) References Cited

U.S. PATENT DOCUMENTS 6,047,861 A 4/2000 Vidal et al.
6,511,457 B2 1/2003 Thompson
(Continued)

FOREIGN PATENT DOCUMENTS

EP 2638868 9/2013
GB 2523591 A * 9/2015 ......... A61B 10/0283
(Continued)

OTHER PUBLICATIONS

SURGIFLO® Hemostatic Matrix Kit—SURGIFLO® and Go, www.jnjmedicaldevices.com, 2022, 5 pages, Ethicon US, LLC.
(Continued)

*Primary Examiner* — Lauren P Farrar

(57) ABSTRACT

A dispensing system includes a hollow tube having an outer wall with an air vent formed in the outer wall. A valve including a flexible flap is disposed inside the tube. The flexible flap, normally biased into a retracted position, is moveable between an extended position for sealing the air vent and the retracted position for unsealing the air vent. A syringe connector interconnects a syringe with the proximal end of the hollow tube and defines a fluid flow path. A flowable viscous fluid is disposed within the syringe. When a syringe plunger is depressed, the flowable viscous fluid is expelled from the syringe and forced through the fluid flow path and into the proximal end of the hollow tube. When the flowable viscous fluid engages the flexible flap, the flexible flap is forced to move into a position that seals the air vent.

17 Claims, 32 Drawing Sheets

(51) Int. Cl.
*A61M 5/31* (2006.01)
*A61M 5/315* (2006.01)

(52) U.S. Cl.
CPC ........ *A61M 5/315* (2013.01); *A61M 25/0074* (2013.01); *A61L 2400/04* (2013.01); *A61M 2005/3123* (2013.01); *A61M 2025/0057* (2013.01); *A61M 2025/0063* (2013.01); *A61M 2025/0079* (2013.01)

(58) Field of Classification Search
CPC ........ A61M 25/0029; A61M 2039/205; A61M 39/105; A61M 25/0097; A61M 2005/3128; A61M 25/0043; A61M 5/3129; A61M 5/315; A61M 25/0074; A61M 2005/3123; A61M 2025/0057; A61M 2025/0063; A61M 2025/0079
See application file for complete search history.

(56) References Cited

U.S. PATENT DOCUMENTS

| | | | | |
|---|---|---|---|---|
| 6,569,145 | B1 * | 5/2003 | Shmulewitz ..... | A61B 17/12022 604/509 |
| 6,733,477 | B2 | 5/2004 | Cowan et al. | |
| 6,926,695 | B2 | 8/2005 | Levinson et al. | |
| 7,037,322 | B1 | 5/2006 | Sing et al. | |
| 8,641,662 | B2 | 2/2014 | Barker, Jr. et al. | |
| 9,179,898 | B2 | 11/2015 | Redl et al. | |
| 2005/0113798 | A1 * | 5/2005 | Slater .................... | A61M 25/10 606/213 |
| 2006/0089603 | A1 * | 4/2006 | Truitt .................... | A61M 39/02 604/246 |
| 2019/0343981 | A1 | 11/2019 | Hammershoj et al. | |

FOREIGN PATENT DOCUMENTS

| | | |
|---|---|---|
| WO | 96/39212 | 12/1996 |
| WO | 2011/151384 | 12/2011 |
| WO | 2011/151386 | 12/2011 |
| WO | 2011/151400 | 12/2011 |
| WO | 2013/185776 | 12/2013 |

OTHER PUBLICATIONS

International Search Report issued in corresponding International Application No. PCT/IB2022/052378, mailed on Jul. 5, 2022, 5 pages.

* cited by examiner

SYSTEMS, DEVICES AND METHODS FOR DISPENSING FLOWABLE HEMOSTATS THAT INCORPORATE SAFETY MECHANISMS FOR PREVENTING AIR EMBOLISMS

CROSS-REFERENCE TO RELATED APPLICATIONS

The present patent application claims benefit of U.S. Provisional Application Ser. No. 63/168,614, filed on Mar. 31, 2021, the disclosure of which is hereby incorporated by reference herein.

BACKGROUND OF THE INVENTION

Field of the Invention

The present patent application is generally related to controlling bleeding at surgical sites and is more particularly related to systems, devices, and methods for dispensing flowable hemostats that are used for controlling bleeding.

Description of the Related Art

Protein-based hemostatic materials such as collagen and gelatin are commercially available in solid sponge and loose or unpacked powder form for use in surgical procedures. Mixing of the loose or unpacked powder with a fluid such as saline or a thrombin solution may form a paste or slurry that is useful as a hemostatic composition for use in cases of diffuse bleeding, particularly from uneven surfaces or hard to reach areas, depending on mixing conditions and relative ratios of the materials.

Conventional hemostatic pastes are usually prepared at the point of use by mechanical agitation and mixing of a biocompatible polymer (e.g., a gelatin), and a liquid (e.g., a thrombin solution), to provide uniformity to the composition. Mixing to form a paste usually requires extensive mixing, such as kneading or transfer between two syringes.

It is often desirable that the hemostatic paste includes a thrombin component to enhance the optimal hemostatic effect of the paste. Due to stability reasons, the thrombin component is usually provided as a dry composition separate from the biocompatible polymer component. The dry thrombin is then reconstituted to form a suspension or solution before mixing with the biocompatible polymer. The reconstitution step of the thrombin component usually takes place immediately prior to mixing with the biocompatible polymer. Reconstitution of thrombin is time consuming and challenging with multi-step syringe handlings involved; factors which are undesirable in an operating room setting with bleedings, as the surgeon will have to pause the procedure while waiting for the hemostat to be prepared.

There have been efforts directed to providing safe and effective flowable hemostats that are used for controlling bleeding. For example, the SURGIFLO® Hemostatic Matrix Kit with Thrombin, sold by Ethicon, Inc. of Somerville, New Jersey, is a kit that is used for producing a hemostatic gelatin paste including thrombin, which is prepared by first reconstituting a dry thrombin composition and subsequently transferring a gelatin matrix-thrombin solution mixture back and forth between two connected syringes for a total of at least six passes.

Other attempts have been made to provide the biocompatible polymer and the thrombin in dry form in the same syringe, such as described in WO 2011/151400, WO 2011/151384, WO 2011/151386 and WO 2013/185776, the disclosures of which are hereby incorporated by reference herein. Due to the sensitivity of thrombin to the sterilization methods usually employed in the manufacture of hemostatic products (i.e., ionizing radiation and/or ethylene oxide), the sensitivity of thrombin to water and the different physical-chemical properties of thrombin and the polymers usually employed, such as gelatin, it has proven challenging to manufacture such “all-in-one” products so that they retain sufficient thrombin activity during manufacturing, sterilization and throughout the shelf-life of the product and/or which ensures satisfactory distribution of thrombin in the final reconstituted hemostatic paste product.

As noted above, incorporating thrombin into hemostatic pastes has proven to be challenging due to either manufacturing or stability reasons or due to time consuming reconstitution of a dry thrombin composition prior to mixing with the biocompatible polymer. Thus, there has been a long-felt need in the art for developing novel methods for quickly and easily incorporating thrombin into a hemostatic paste, and for simple and fast methods for preparing a hemostatic composition in the operating room where potential bleeding must be controlled in a fast and efficient manner.

In response, US 2019/0343981, assigned to Ethicon, Inc., the disclosure of which is hereby incorporated by reference herein, teaches a method for preparing a hemostatic composition that includes thrombin. In one embodiment, the method includes the step of reconstituting a dry thrombin directly in a paste, such as a paste comprising a biocompatible polymer. The hemostatic composition including the thrombin may be prepared from a dry thrombin composition and a paste in a single step. The flowable hemostat is used for treating a wound (e.g., controlling bleeding).

Referring to FIG. 26, a system for controlling bleeding at a surgical site includes an applicator device 50 for dispensing a flowable hemostat, such as the flowable hemostat matrix with Thrombin sold under the trademark SURGIFLO®, by Ethicon, Inc. of Somerville, New Jersey The applicator device includes a syringe 52 that contains a flowable hemostat 54 and an applicator tip 56 that is secured to a distal end of the syringe 52. A syringe plunger 58 may be depressed for dispensing the flowable hemostat 54 from a distal end 60 of the applicator tip 56.

In FIG. 27A, a vessel V has a wound W that is bleeding. The distal end 60 of the applicator tip 56 is juxtaposed with the bleeding wound site to apply the flowable hemostat 54 over the wound W.

FIG. 27B shows the bleeding wound site after it has been fully covered by a mass of the flowable hemostat 54. The flowable hemostat helps in blood clotting by speeding up the conversion of a substance in the blood called fibrin, to fibrinogen. This chemical reaction leads to the formation of blood clots, which is the final step in the process of hemostasis.

In some instances, a residual amount of the flowable hemostat remains within the cannula of the applicator tip 56. To eliminate waste and use a higher percentage of the flowable hemostat that has been prepared, it is desirable if the residual amount of the flowable hemostat that remains within the applicator tip 56 can be dispensed from the distal end 60 of the dispensing device. In some instances, the distal end of the syringe is detached from a proximal end of the applicator tip 56, and a stylus or stick is inserted into the cannula of the applicator tip to force the residual or stranded flowable hemostat from the distal end of the applicator tip. This extra step during a surgical procedure wastes time and forces the surgeon to remove his or her eyes from the surgical site as they focus on advancing a stick through the cannula to expel the stranded flowable hemostat from the distal end of the applicator tip.

Despite the above advances, there remains a need for improved systems, devices, and methods for efficiently and safely dispensing flowable hemostats at surgical sites for promoting blood clotting and controlling bleeding. There also remains a need for improved systems, devices, and methods of expelling residual amounts of flowable hemostats that remain stranded adjacent the distal ends of applicator tips. There also remains a need for flowable hemostat dispensing devices that have safety mechanisms such as air embolism prevention assemblies incorporated therein for preventing air embolisms.

SUMMARY OF THE INVENTION

In one embodiment, after a flowable hemostat (e.g., a flowable hemostat sold by Ethicon, Inc. of Somerville, New Jersey under the trademark SURGIFLO® Hemostatic Matrix Kit with Thrombin) has been dispensed from a distal end of a hollow tube (e.g., an applicator tip), a non-insignificant, residual amount of the flowable hemostat material may remain within the cannula of the applicator tip.

In one embodiment, the residual amount of the flowable hemostat that remains within the distal end of the hollow tube may be pushed out of the distal end of the hollow tube by forcing air into the proximal end of the hollow tube. In one embodiment, the air pressure expels the remaining flowable hemostat from the distal end of the hollow tube.

In one embodiment, to prevent air from exiting at the distal opening of the hollow tube, which can cause an air embolism, the system disclosed herein includes an air release valve that extends through an outer wall of the hollow tube. In one embodiment, as the flowable hemostat flows through the hollow dispensing tube, the valve is closed when the flowable hemostat contacts the valve, however, the valve moves back to an open position once the flowable hemostat has passed by the valve and no longer contacts the valve. At that stage, with the valve in the open position, any air that is forced into the hollow tube to expel the residual flowable hemostat may be safely released through an air vent formed in an outer wall of the hollow tube, thereby preventing the formation of air embolisms.

In one embodiment, a system for dispensing a flowable hemostat preferably includes an air embolism prevention mechanism incorporated into a hollow dispensing tube (e.g., an applicator tip). In one embodiment, the air embolism prevention mechanism preferably includes the hollow tube having one or more air vents and a valve with one or more flexible flaps that are located inside of the hollow tube.

In one embodiment, the flexible flaps are initially open (i.e., biased in the open position) for unsealing the air vents of the hollow tube. When the flowable hemostat engages the flaps as it flows through the valve, the flowable hemostat engages the flexible flaps and forces the flexible flaps to move into a closed position for sealing the air vents.

After dispensing flowable hemostat with a syringe, air may be forced into the proximal end of the hollow tube to push out flowable hemostat that remains within the hollow tube. Once the flowable hemostat fully passes through the valve and no longer contacts the flexible flaps, the flexible flaps will spring back to the open position for seating the air vents. The air that is used to push out the remaining flowable hemostat exits through the unsealed air vents that are formed in the outer wall of the hollow tube instead of exiting from the opening at the distal end of the hollow tube, thereby preventing the formation of air embolisms.

In one embodiment, a cannula for delivering a flowable hemostat (e.g., a viscous fluid, a paste, gelatin, SURGIFLO® Hemostatic Matrix kit with Thrombin) may include an elongated hollow tube having a proximal end connected to a source of the flowable hemostat and having an expression port at a distal end of the elongated hollow tube. A normally open valve including a flexible flap is disposed inside the cannula and is attached to an inside wall of the hollow tube.

In one embodiment, the valve is configured to close and cover an air vent (e.g., an air release opening) that is formed in an outer wall of the hollow tube. As the flowable hemostat passes by the flexible flap, the flowable hemostat forces the flexible flap to move into a closed position in which it touches an inner surface of the hollow tube for closing and/or sealing the air vent opening.

In one embodiment, once the flowable hemostat has passed by the flap and/or is not touching the flap, the valve is configured to open. In one embodiment, when air is forced into the hollow tube to expel any residual of the flowable hemostat that remains inside the hollow tube, the open flap allows the air to be released from the air vent formed in the hollow tube.

In one embodiment, a system for dispensing a flowable hemostat preferably includes a hollow tube having an outer wall that extends from a proximal end to a distal end of the hollow tube.

In one embodiment, at least one air vent is formed in the outer wall of the hollow tube. In one embodiment, the at least one air vent is preferably adjacent the distal end of the hollow tube.

In one embodiment, a valve including at least one flexible flap is desirably disposed inside the hollow tube. The at least one flexible flap is moveable between a first position for unsealing the at least one vent and a second position for sealing the at least one air vent. In one embodiment, the valve is open when the flexible flap is in the first position and the valve is closed when the flexible flap is in the second position.

In one embodiment, the at least one flexible flap is normally biased into the first position (i.e., the open position) for unsealing the at least one air vent. If the flexible flap is forced into the closed position, it will spring back to the open position once the force from the flowable hemostat is removed.

In one embodiment, the at least one air vent may include two or more air vents that are formed in the outer wall of the hollow tube.

In one embodiment, the at least one flexible flap may include two or more flexible flaps, whereby each flexible flap is configured for sealing and unsealing an air vent associated therewith.

In one embodiment, the at least one air vent may include four air vents that are formed in the outer wall of the hollow tube. In one embodiment, the four air vents are evenly spaced from one another adjacent the distal end of the hollow tube.

In one embodiment, the at least one flexible flap may include a first flexible flap that is configured for sealing and unsealing a first air vent, a second flexible flap that is configured for sealing and unsealing a second air vent, a third flexible flap that is configured for sealing and unsealing a third air vent, and a fourth flexible flap that is configured for sealing and unsealing a fourth air vent.

In one embodiment, a valve may include a valve ring having a proximal edge and a distal edge.

In one embodiment, the four flexible flaps preferably have proximal ends that are hingedly connected with the distal edge of the valve ring, which enables the flaps to move between retracted positions (i.e., the open position for venting air) and extended positions (i.e., the closed position for sealing the air vents).

In one embodiment, the valve ring and the four flexible flaps are preferably disposed inside the hollow tube so that the four flexible flaps are distal to the valve ring and so that the four flexible flaps are aligned with the four air vents, respectively.

In one embodiment, the four flexible flaps may be evenly spaced from one another around a perimeter of the valve ring.

In one embodiment, the inside of the hollow tube may have a structure that engages the valve for properly aligning the valve relative to the one or more air vents and/or for securing the valve in place inside the hollow tube so that it does not inadvertently shift and/or move once it has been secured inside the hollow tube.

In one embodiment, at least one stop may be disposed inside the hollow tube. The stop may project inwardly from an inner surface of the outer wall of the hollow tube.

In one embodiment, the distal edge of the valve ring may be in contact with the at least one stop for securing and/or aligning the valve in place inside the hollow tube.

In one embodiment, a dispensing system may include a syringe having a syringe barrel and a syringe plunger that is disposed inside the syringe barrel. In one embodiment, the syringe is adapted for receiving a flowable hemostat that is dispensed from a distal end of the hollow tube.

In one embodiment, the system may include a syringe connector having a proximal end coupled with a distal end of the syringe barrel and a distal end coupled with the proximal end of the hollow tube.

In one embodiment, the syringe connector desirably has a fluid conduit that extends from the proximal end to the distal end of the syringe connector to define a fluid flow path between the syringe barrel and the hollow tube.

In one embodiment, the dispensing system may include a one-way fluid valve disposed within the fluid flow path of the syringe connector that permits the flowable hemostat to flow in a distal direction while preventing backflow of the flowable hemostat in a proximal direction.

In one embodiment, the dispensing system may include a first air inlet formed in the syringe connector that intersects with the fluid flow path.

In one embodiment, a first one-way air valve may be disposed in the first air inlet that allows air to flow inwardly from the first air inlet to the fluid flow path while preventing the air from flowing outwardly from the fluid flow path to the first air inlet.

In one embodiment, the dispensing system may include a second air inlet formed in the syringe connector that intersects with the fluid flow path.

In one embodiment, a second one-way air valve may be disposed in the second air inlet that allows air to flow inwardly from the second air inlet to the fluid flow path while preventing the air from flowing outwardly from the fluid flow path to the second air inlet.

In one embodiment, the first and second air inlets have inner ends that intersect with the fluid flow path at a section of the fluid flow path that is located between the one-way fluid valve and the proximal end of the syringe connector.

In one embodiment, the dispensing system desirably includes a flowable viscous fluid, such as a flowable hemostat (e.g., SURGIFLO® Hemostatic Matrix Kit with Thrombin), that is disposed within the syringe barrel. In one embodiment, depressing the syringe plunger toward the distal end of the syringe barrel preferably expels the flowable viscous fluid from the syringe barrel and forces the flowable viscous fluid through the fluid flow path of the syringe connector and into the proximal end of the elongated hollow tube.

In one embodiment, a system for dispensing a flowable viscous fluid desirably includes an elongated hollow tube having a proximal end, a distal end, an outer wall that extends from the proximal end to the distal end of the elongated hollow tube, and at least one an air vent formed in the outer wall that is located adjacent the distal end of the elongated hollow tube.

In one embodiment, the dispensing system preferably includes a valve having at least one flexible flap, which is disposed inside the elongated hollow tube.

In one embodiment, the at least one flexible flap is moveable between an extended position (i.e., the closed position) for sealing the at least one air vent and a retracted position (i.e., the open position) for unsealing the at least one air vent.

In one embodiment, the at least one flexible flap is normally biased into the retracted position for unsealing the at least one air vent.

In one embodiment, the system includes a syringe having a syringe barrel and a syringe plunger that is disposed inside the syringe barrel.

In one embodiment, the system preferably includes a syringe connector having a proximal end coupled with a distal end of the syringe barrel and a distal end coupled with the proximal end of the elongated hollow tube.

In one embodiment, the syringe connector preferably has a fluid conduit that extends from the proximal end to the distal end of the syringe connector, which defines a fluid flow path that extends between the syringe barrel and the elongated hollow tube.

In one embodiment, a flowable viscous fluid is disposed within the syringe barrel.

In one embodiment, the syringe plunger is adapted for being depressed toward the distal end of the syringe barrel for expelling the flowable viscous fluid from the syringe barrel and forcing the flowable viscous fluid through the fluid flow path of the syringe connector and into the proximal end of the elongated hollow tube.

In one embodiment, the at least one air vent may include four air vents that are formed in the outer wall of the hollow tube and that are evenly spaced from one another adjacent the distal end of the hollow tube.

In one embodiment, the at least one flexible flap may include a first flexible flap that is configured for sealing and unsealing a first air vent, a second flexible flap that is configured for sealing and unsealing a second air vent, a third flexible flap that is configured for sealing and unsealing a third air vent, and a fourth flexible flap that is configured for sealing and unsealing a fourth air vent.

In one embodiment, the valve preferably includes a valve ring having a proximal edge and a distal edge.

In one embodiment, the four flexible flaps have proximal ends that are hingedly connected with the distal edge of the valve ring.

In one embodiment, the valve ring and the four flexible flaps are disposed inside the elongated hollow tube so that the four flexible flaps are distal to the valve ring and so that the four flexible flaps are aligned with the four air vents, respectively.

In one embodiment, the four flexible flaps are preferably evenly spaced from one another around a perimeter of the valve ring.

In one embodiment, the dispensing system may include a one-way fluid valve disposed within the fluid flow path of the syringe connector that permits fluid to flow in a distal direction while preventing backflow of the fluid in a proximal direction.

In one embodiment, an air inlet may be formed in the syringe connector that intersects with the fluid flow path, and a one-way air valve may be disposed in the air inlet that allows air to flow inwardly from the air inlet to the fluid flow path while preventing the air from flowing outwardly from the fluid flow path to the air inlet.

In one embodiment, the air inlet preferably has an inner end that intersect with the fluid flow path at a section of the fluid flow path that is located between the one-way fluid valve and the proximal end of the syringe connector.

In one embodiment, a method of dispensing a flowable viscous fluid preferably includes obtaining a hollow tube having an outer wall with at least one air vent formed in the outer wall at a location that is adjacent a distal end of the hollow tube, whereby the hollow tube includes a valve having at least one flexible flap disposed inside the hollow tube that is normally biased in an open position for unsealing the at least one air vent.

In one embodiment, a method of dispensing a flowable viscous fluid preferably includes forcing a mass of a flowable viscous fluid into the hollow tube and toward a distal end of the hollow tube until the mass of the flowable viscous material engages the at least one flexible flap for forcing the at least one flexible flap to move into a closed position for sealing the at least one air vent.

In one embodiment, the method may include, after the forcing the mass step, directing air into a proximal end of the hollow tube whereupon the air forces the mass of the flowable viscous fluid to move in a distal direction beyond a distal end of the at least one flexible flap so that the air engages the at least one flexible flap whereupon the at least one flexible flap moves into an open position for unsealing the at least one air vent.

In one embodiment, the at least one air vent may include four air vents that are formed in the outer wall of the hollow tube and that are evenly spaced from one another adjacent the distal end of the hollow tube.

In one embodiment, the at least one flexible flap may include a first flexible flap that is configured for sealing and unsealing a first air vent, a second flexible flap that is configured for sealing and unsealing a second air vent, a third flexible flap that is configured for sealing and unsealing a third air vent, and a fourth flexible flap that is configured for sealing and unsealing a fourth air vent.

These and other preferred embodiments will be described in more detail below.

DETAILED DESCRIPTION OF PREFERRED EMBODIMENTS

Definitions

"Biocompatible" refers to a material's ability to perform its intended function without eliciting any substantial undesirable local or systemic effects in the host.

A "flowable hemostat" is a composition that is designed to actively help in blood clotting. Flowable hemostats speed up the conversion of a substance in the blood called fibrin, to fibrinogen. This chemical reaction leads to the formation of blood clots, which is the final step in the process of hemostasis. Flowable hemostats are made of a mostly liquid mixture of biomaterials like gelatin and cellulose mixed with thrombin. An example of a flowable hemostat is sold by Ethicon, Inc. of Somerville, New Jersey under the trademark SURGIFLO® Hemostat Matrix Kit with Thrombin.

"Hemostasis" is a process which causes bleeding to diminish or stop. Hemostasis occurs when blood is present outside of the body or blood vessels and is the instinctive response for the body to stop bleeding and loss of blood. During hemostasis three steps occur in a rapid sequence. Vascular spasm is the first response as the blood vessels constrict to allow less blood to be lost. In the second step, platelet plug formation, platelets stick together to form a temporary seal to cover the break in the vessel wall. The third and last step is called coagulation or blood clotting. Coagulation reinforces the platelet plug with fibrin threads that act as a "molecular glue." A hemostatic compound, such as the flowable hemostat sold by Ethicon, Inc. of Somerville, New Jersey under the trademark SURGIFLO® Hemostat Matrix Kit with Thrombin, is capable of stimulating hemostasis.

Figure 1:
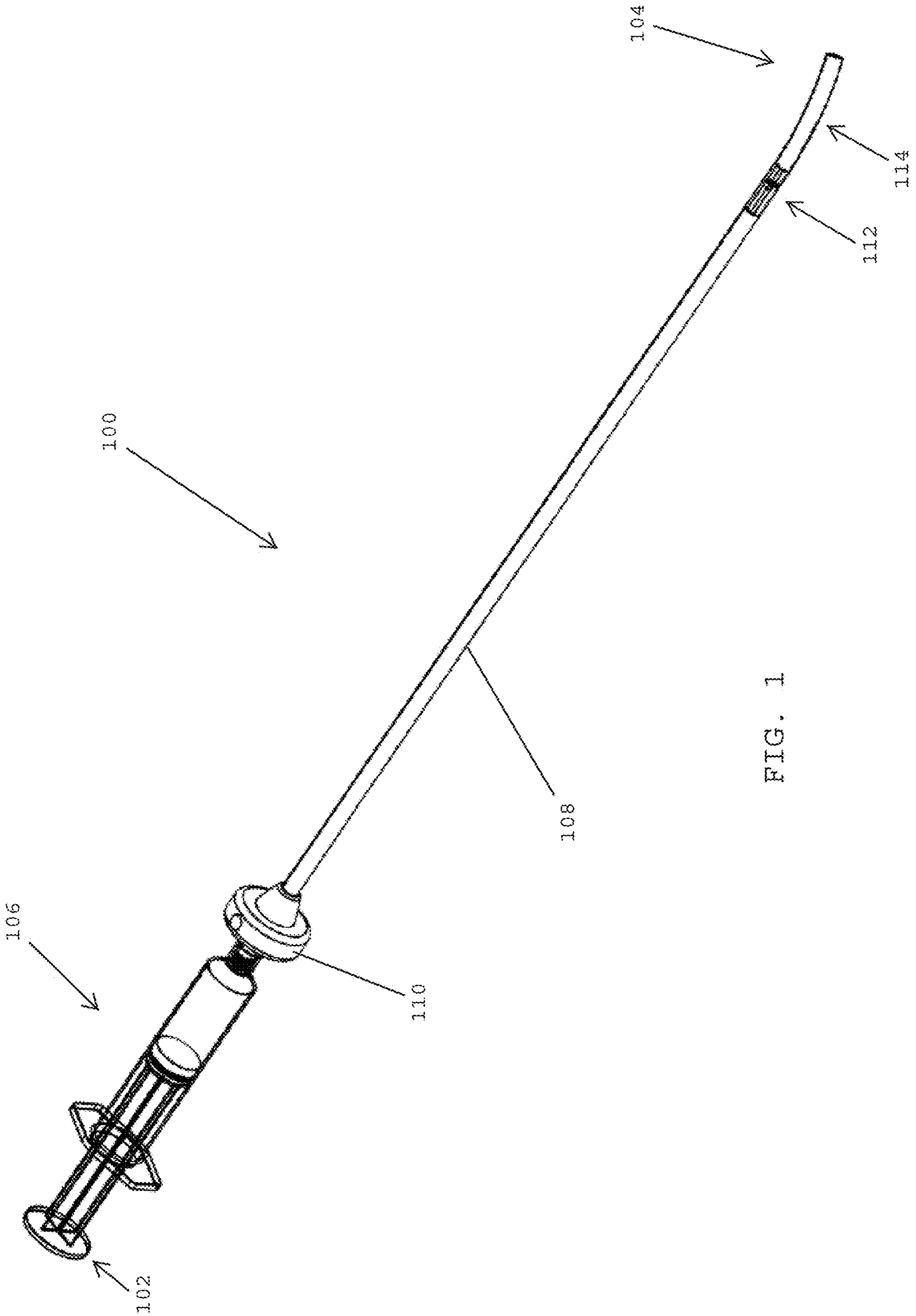
FIG. 1 is a perspective view of a dispensing device for dispensing a flowable hemostat, the dispensing device having an air embolism prevention assembly, in accordance with one embodiment of the present patent application.

Referring to FIG. 1, in one embodiment, a dispensing device 100 for dispensing a flowable hemostat (e.g., the flowable hemostat sold by Ethicon, Inc. of Somerville, New Jersey under the trademark SURGIFLO® Hemostat Matrix Kit with Thrombin) preferably has a proximal end 102 and a distal end 104. In one embodiment, the dispensing device 100 desirably includes a syringe 106 that is adapted to dispense a flowable hemostat, an elongated dispensing tube 108, a syringe connector 110 that connects a distal end of the syringe 106 with a proximal end of the elongated dispensing tube 108, an air embolism prevention assembly 112 connected with a distal end of the elongated dispensing tube 108, and a dispensing tip 114 connected with a distal end of the air embolism prevention assembly 112.

In one embodiment, the elongated dispensing tube 108 may be made of a biocompatible material such as stainless steel. In one embodiment, the elongated dispensing tube 108, the air embolism prevention assembly 112, and the dispensing tip 114 may be joined together by press fitting the components together (e.g., different outer diameters) and/or by using an adhesive. In one embodiment, the elongated dispensing tube 108, the air embolism prevention assembly 112, and the dispensing tip 114 may be joined together into a single component that may be referred to as a hollow tube or an applicator tip. In one embodiment, the air embolism prevention assembly 112 may be an integrally formed part of the elongated dispensing tube 108 or the above-described hollow tube or applicator tip.

Figure 2:
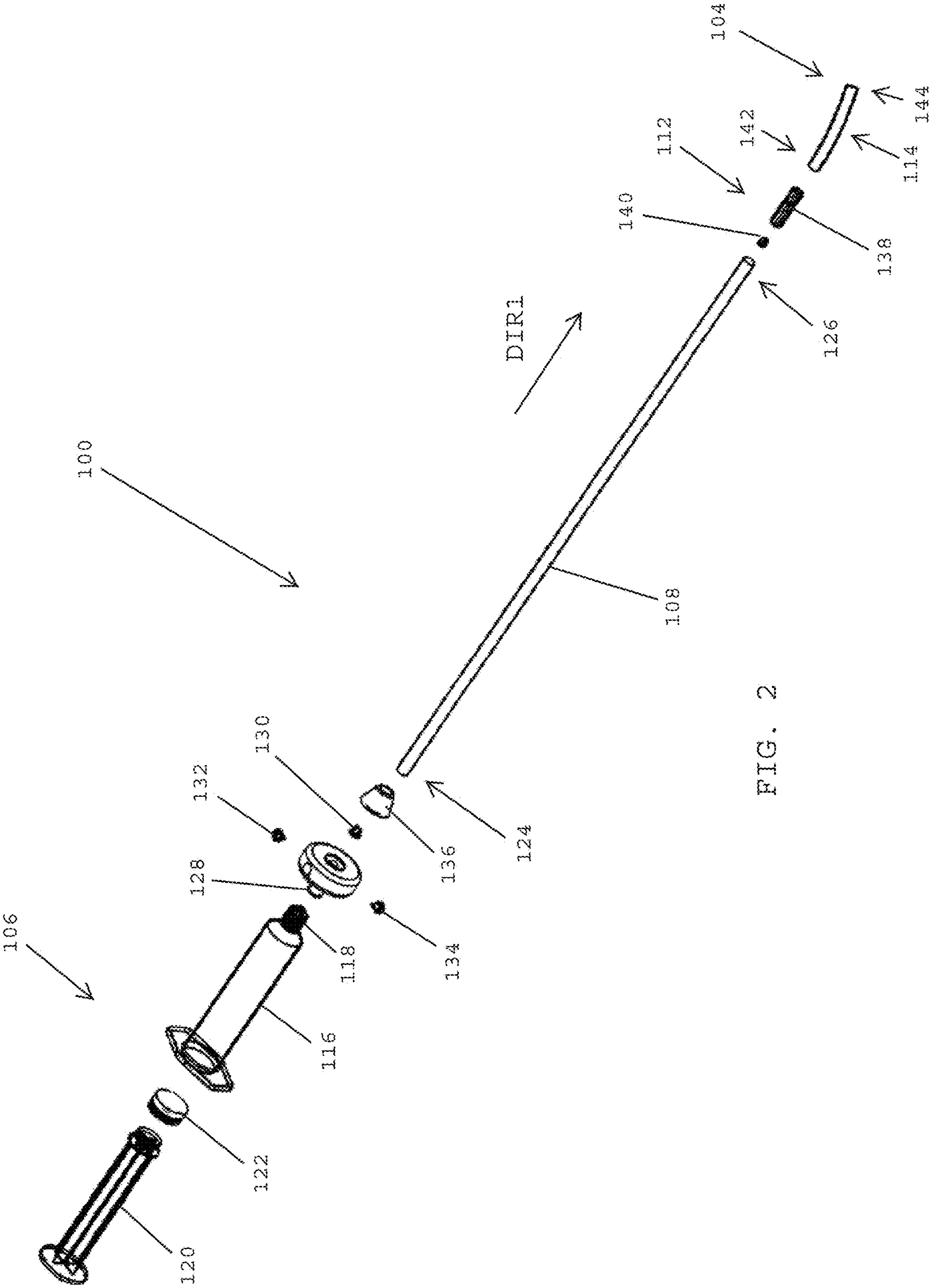
FIG. 2 is an exploded view of the dispensing device shown in FIG. 1.

Referring to FIG. 2, in one embodiment, the syringe 106 preferably includes a syringe barrel 116 having a distal tip 118, a syringe plunger 120 that is adapted to be inserted inside the syringe barrel 116 for forcing a flowable hemostat through the distal tip 118, and a syringe seal 122 that is adapted to be secured to the distal end of the syringe plunger 120. In one embodiment, a flowable hemostat (e.g., SURGIFLO®) may be disposed within the syringe barrel 116 of the syringe 106.

In one embodiment, the elongated dispensing tube 108 preferably has a proximal end 124 and a distal end 126. The elongated dispensing tube 108 preferably includes an elongated conduit that extends from the proximal end 124 to the distal end 126 for enabling a flowable hemostat to be passed through the elongated dispensing tube 108.

In one embodiment, the dispensing device 100 preferably includes the syringe connector 110 that is utilized for interconnecting the distal tip 118 of the syringe barrel 116 with the proximal end 124 of the elongated dispensing tube 108. In one embodiment, the syringe connector 110 preferably includes an attachment post 128 that is adapted to be inserted into an opening of the distal tip 118 of the syringe barrel 116. In one embodiment, threads may be utilized for securing the distal tip 118 of the syringe barrel 116 with the attachment post 128 of the syringe connector 110. The distal tip 118 and the attachment post 128 preferably form a fluid-tight seal that enables a flowable hemostat to be directed from the syringe barrel 116 and into the syringe connector 110.

In one embodiment, the dispensing device 100 preferably includes a one-way fluid valve 130 that is configured to enable a flowable hemostat to flow in only the distal direction DIR1 toward the distal end 104 of the dispensing device.

In one embodiment, the flowable hemostat dispensing device 100 preferably includes a first one-way air valve 132 and a second one-way air valve 134 that are configured to enable air to be drawn into the syringe connector 110 and the syringe barrel 116, as will be described in more detail herein.

In one embodiment, the dispensing device 100 preferably includes a tube connector 136 that is adapted to interconnect a distal end of the syringe connector 110 with the proximal end 124 of the elongated dispensing tube 108. In one embodiment, the tube connector 136 preferably forms a fluid-tight seal between the syringe connector 110 and the proximal end 124 of the elongated dispensing tube 108.

In one embodiment, the dispensing device 100 preferably includes the air embolism prevention assembly 112 having a fluid regulating safety tube 138 and a valve 140 that is configured to be disposed inside the fluid regulating safety tube 138. In one embodiment, the air embolism prevention assembly is desirably disposed between the distal end 126 of the elongated dispensing tube 108 and the proximal end 142 of the dispensing tip 114. In one embodiment, the air embolism prevention assembly may be incorporated into the elongated dispensing tube 108 or into a single hollow tube that combines the elongated dispensing tube 108, the air embolism prevention assembly 112 and the dispensing tip 114.

In one embodiment, the flowable hemostat dispensing device 100 desirably includes the dispensing tip 114 that is configured for dispensing the flowable hemostat from the distal end 104 of the hemostat fluid dispensing device 100. In one embodiment, the dispensing tip 114 has a proximal end 142 and a distal end 144 with an elongated conduit extending from the proximal end 142 to the distal end 144. In one embodiment, the proximal end 142 of the dispensing tip 114 is secured to a distal end of the fluid regulating safety tube 138. In one embodiment, the dispensing tip 114 may be rigid. In one embodiment, the dispensing tip 114 may be made of a flexible material.

Figure 3:
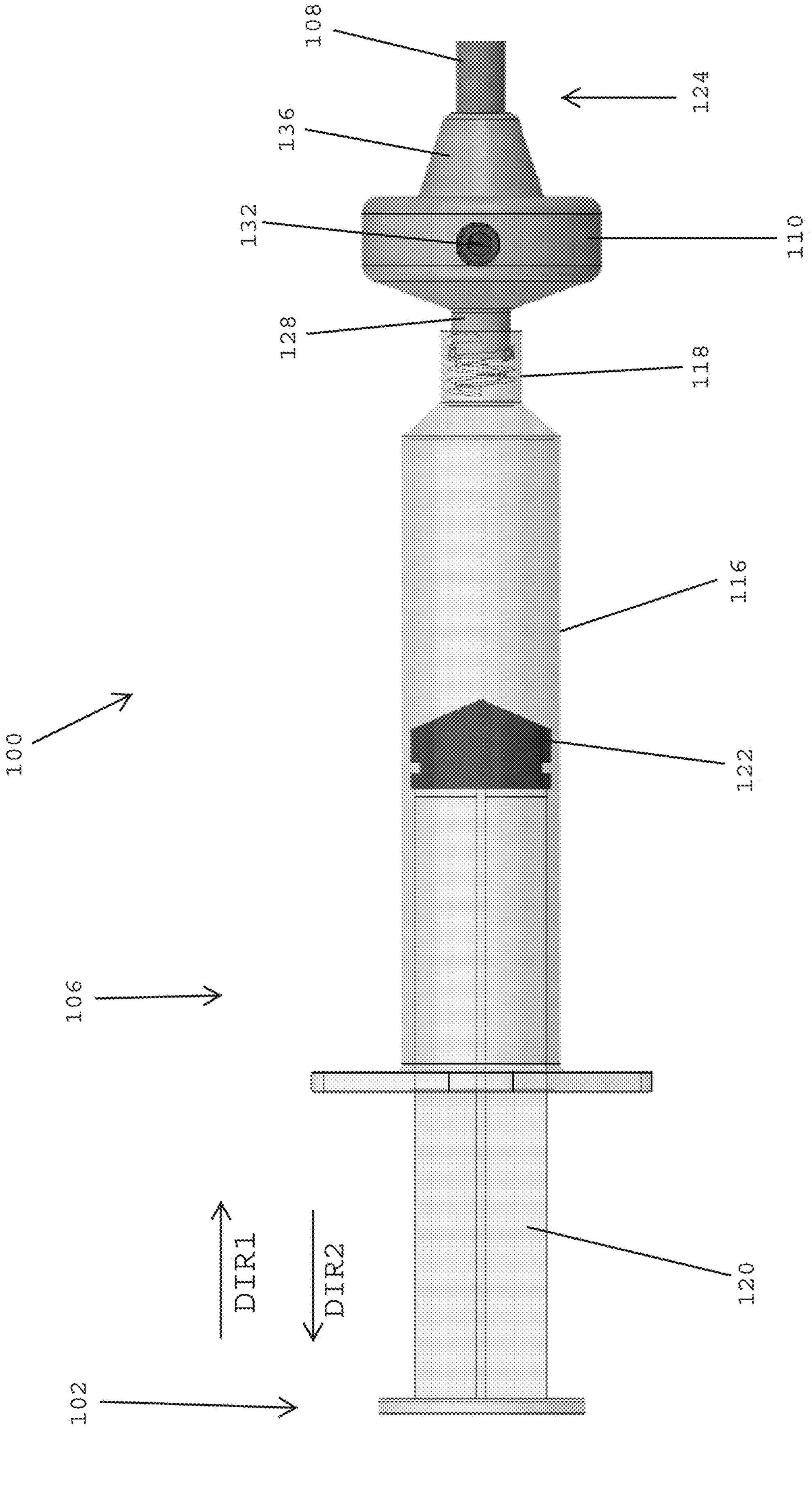
FIG. 3 is a top view of a proximal end of the dispensing device shown in FIG. 1.
Figure 4:
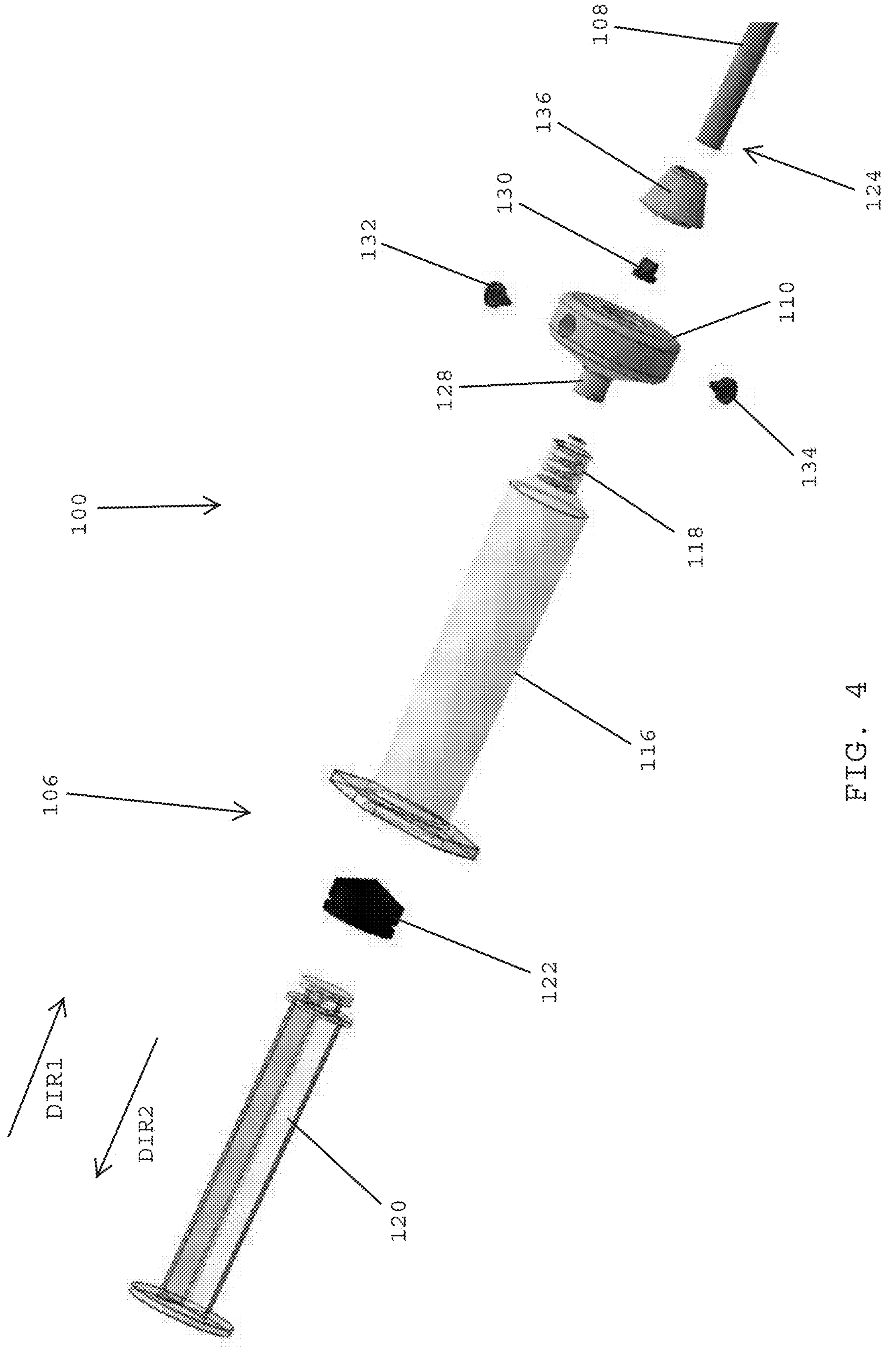
FIG. 4 is an exploded view of the proximal end of the dispensing device shown in FIG. 3.

Referring to FIGS. 3 and 4, in one embodiment, the proximal end 102 of the dispensing device 100 preferably includes the syringe 106 having the syringe barrel 116, the syringe plunger 120 that is inserted into the syringe barrel 116, and the syringe seal 122 that is secured to a distal end of the syringe plunger 120.

The distal end of the syringe barrel 116 preferably includes the distal tip 118. In one embodiment, the distal tip 118 has an opening than enables a flowable hemostat to de dispensed from the distal end of the syringe barrel 116. In one embodiment, the distal tip 118 has internal threads that are adapted to mesh with external threads provided on the attachment post 128 of the syringe connector 110. The syringe connector 110 preferably includes the first one-way air valve 132. In one embodiment, when the syringe plunger 120 is pulled in the proximal direction DIR2, air may be drawn through the first one-way air valve and the syringe connector 110 for being stored in the syringe barrel 116 of the syringe 106.

In one embodiment, the dispensing device 100 preferably includes the tube connector 136 that is secured to the distal end of the syringe connector 110 and that is utilized for coupling the proximal end 124 of the elongated dispensing tube 108 with the syringe connector 110. In one embodiment, the tube connector 136 forms a fluid-tight seal between the syringe connector 110 and the proximal end 124 of the elongated dispensing tube 108.

Referring to FIG. 4, in one embodiment, the one-way fluid valve 130 is preferably positioned between the distal end of the syringe connector 110 and the tube connector 136. The one-way fluid valve 130 desirably enables the flowable hemostat and/or air to flow through the one-way fluid valve in the distal direction DIR1, however, the one-way fluid valve 130 prevents the flowable hemostat and the air from flowing through the one-way fluid valve in the proximal direction DIR2.

In one embodiment, the dispensing device 100 preferably includes the first and second one-way air valves 132, 134, which are coupled with the syringe connector 110 for enabling air to be drawn through the syringe connector and into the syringe barrel 116 when the syringe plunger 120 is pulled in the proximal direction DIR2.

Figure 5:
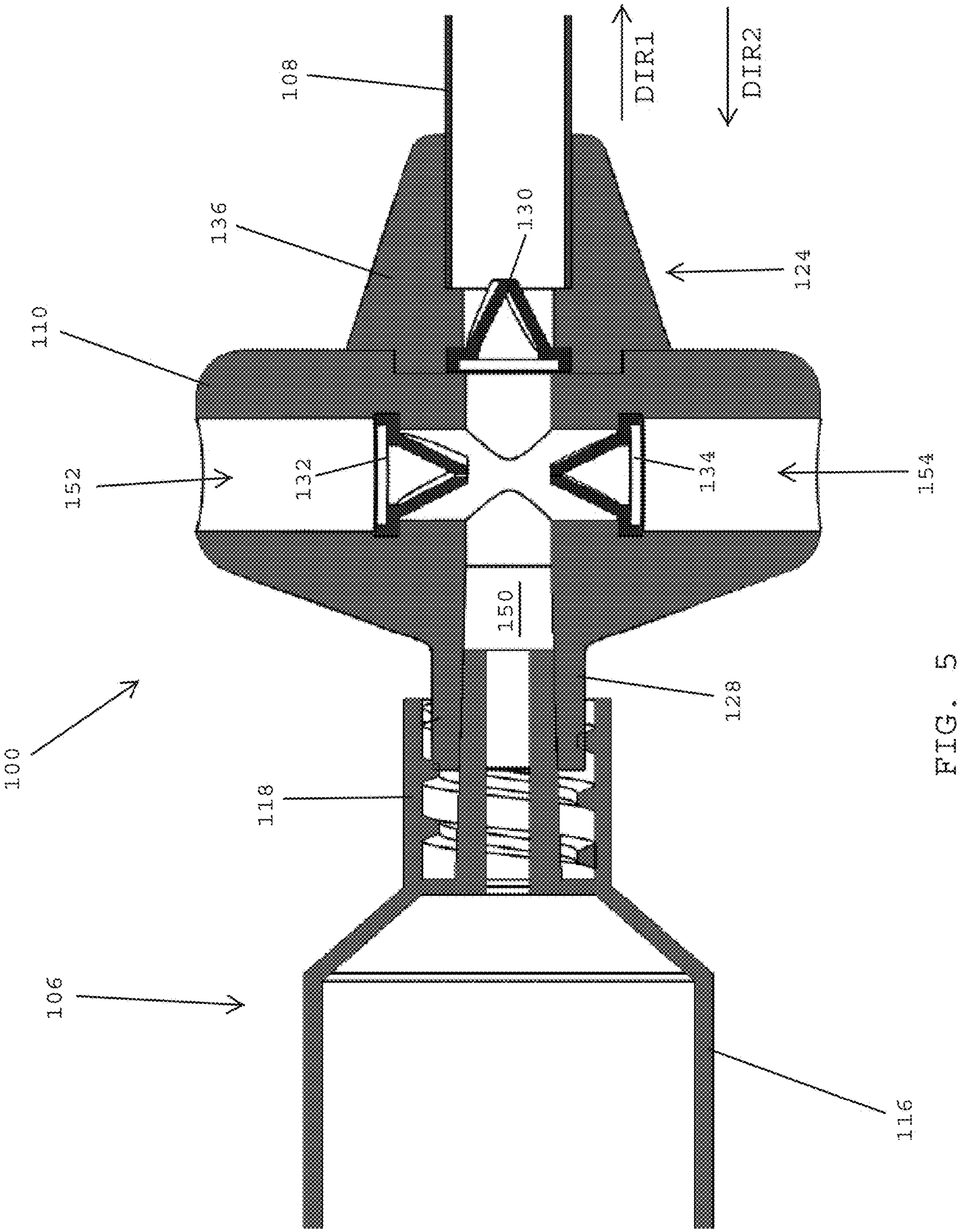
FIG. 5 is a cross-sectional view of a syringe connector of a dispensing device for dispensing a flowable hemostat, in accordance with one embodiment of the present patent application.

Referring to FIG. 5, in one embodiment, the syringe connector 110 is utilized for interconnecting the distal tip 118 of the syringe barrel 116 with the proximal end 124 of the elongated dispensing tube 108, thereby enabling the flowable hemostat to flow from the syringe barrel 116 to the elongated dispensing tube 108. In one embodiment, the distal tip 118 of the syringe barrel 116 desirably has internal threads that are adapted to mesh with external threads on the attachment post 128 of the syringe connector 110 for securing the distal end of the syringe barrel 116 with the attachment post 128 of the syringe connector.

In one embodiment, the tube connector 136 preferably couples the proximal end 124 of the elongated dispensing tube 108 with the distal face of the syringe connector 110. The tube connector 136 preferably forms a fluid-tight seal between the syringe connector 110 and the elongated dispensing tube 108.

In one embodiment, the syringe connector 110 preferably includes a fluid conduit 150 that extends from the proximal end to the distal end of the syringe connector for directing the flowable hemostat material from the syringe barrel 116 and into the proximal end 124 of the elongated dispensing tube 108. In one embodiment, the one-way fluid valve 130 is disposed within the fluid conduit 150 for allowing the flowable hemostat to flow in only the distal direction DIR1 but preventing the flowable hemostat from reversing direction and flowing in the opposite, proximal direction DIR2. As a result, the flowable hemostat can flow distally through the one-way fluid valve 130, however, the one-way fluid valve 130 prevents the flowable hemostat from reversing direction and/or backing up and flowing in the proximal direction DIR2 through the one-way fluid valve 130.

In one embodiment, the syringe connector preferably includes a first air inlet 152 and a second air inlet 154, which are configured for drawing ambient air into the syringe connector.

In one embodiment, the first one-way air valve 132 is disposed within the first air inlet 152 and the second one-way air valve 134 is disposed within the second air inlet 154.

In one embodiment, when the syringe plunger is pulled and/or withdrawn in the proximal direction DIR2, ambient air that surrounds the syringe connector 110 is drawn through the first and second air inlets 152, 154 and through the respective first and second one-way air valves 132, 134 for being drawn into the enclosed chamber of the syringe barrel 116. After air has been drawn into the syringe barrel 116, depressing the syringe plunger in the distal direction DIR1 will force the air into the fluid conduit 150 of the syringe connector 110, through the one-way fluid valve 130 that is disposed within the fluid conduit, and into the proximal end 124 of the elongated dispensing tube 108. As the air is being forced in the distal direction DIR1 through the one-way fluid valve 130, the first and second one-way air valves 132, 134 block the air from passing through the first and second one-way air valves for being discharged through the respective first and second air inlet openings 152, 154 of the syringe connectors 110.

In the prior art, a component similar in function and structure to the syringe connector does not have air inlets formed therein. As a result, when using prior art devices, surgeons must first disconnect a syringe barrel from the proximal end of the elongated dispensing tube 108 to be able to draw air into the syringe barrel 116. In contrast, in the embodiments disclosed in the present patent application, when desiring to draw air into the syringe barrel, surgeons can leave the syringe barrel attached to the syringe connector because the air inlets 152, 154 enable air to be drawn into the syringe connector while the syringe connector remains attached to the syringe barrel 116.

Figure 6A:
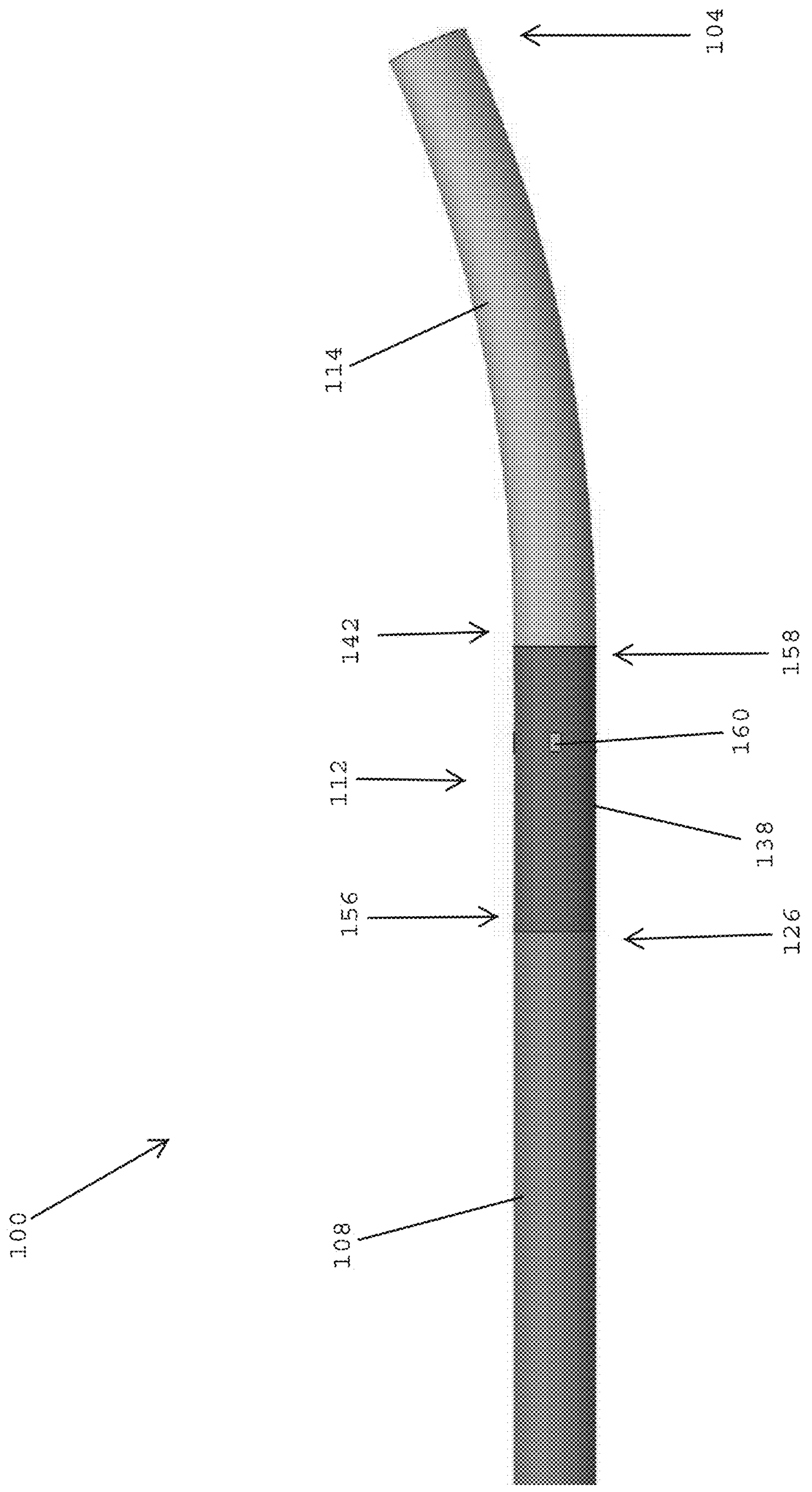
FIG. 6A is a side view of a distal end of a dispensing device for dispensing a flowable hemostat, the dispensing device including an air embolism prevention assembly, in accordance with one embodiment of the present patent application.
Figure 6B:
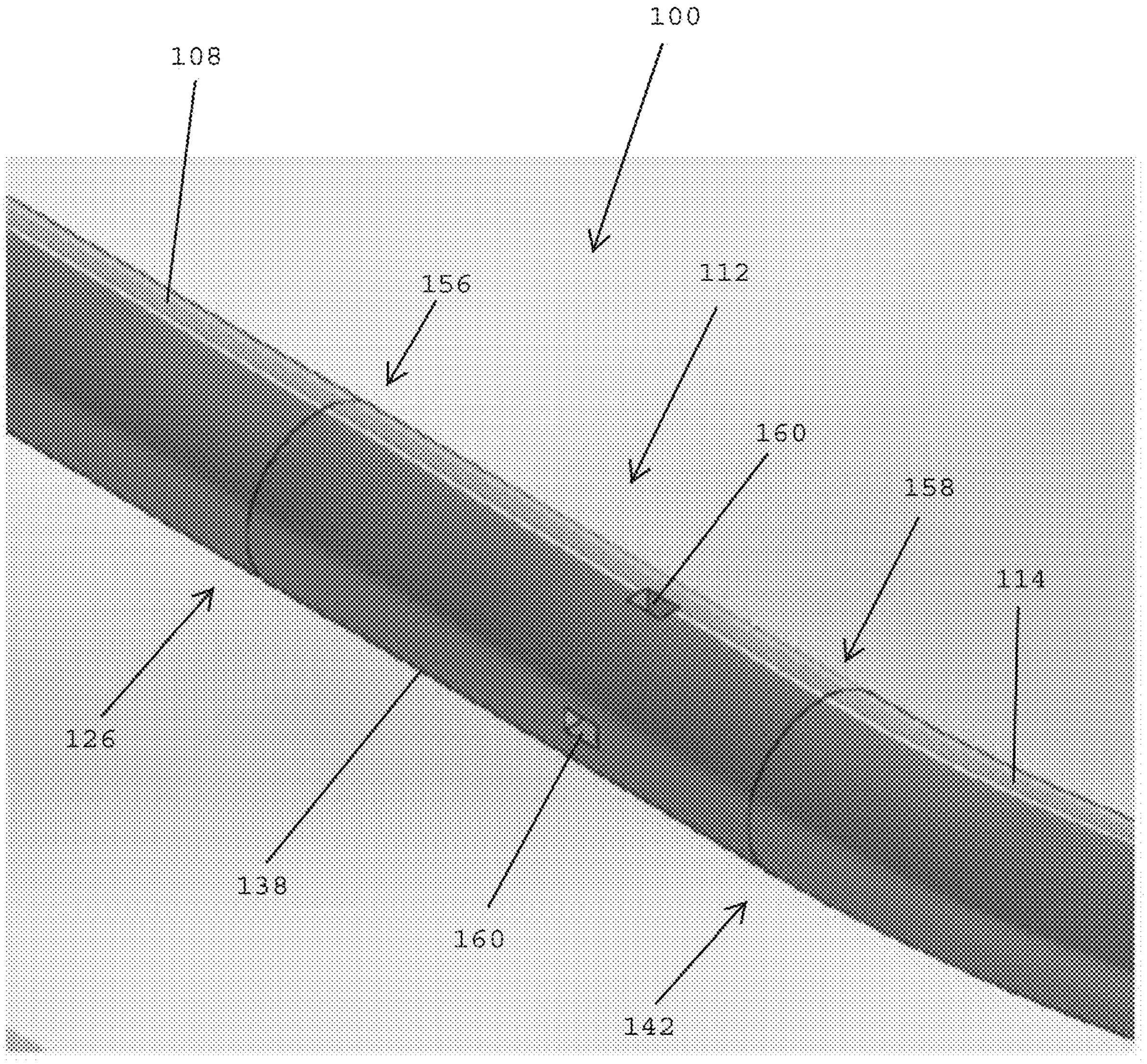
FIG. 6B is a magnified, perspective view of the air embolism prevention assembly shown FIG. 6A.

Referring to FIGS. 6A and 6B, in one embodiment, the flowable hemostat dispensing device 100 preferably includes the air embolism prevention assembly 112 that is located adjacent the distal end 104 of the dispensing device. In one embodiment, the air embolism prevention assembly 112 includes the fluid regulating safety tube 138 having a proximal end 156 connected with the distal end 126 of the elongated dispensing tube 108 and a distal end 158 connected with the proximal end 142 of the dispensing tip 114.

In one embodiment, the fluid regulating safety tube 138 preferably includes one or more air vent openings 160 that are formed in the outer wall of the fluid regulating safety tube 138. As will be described in more detail herein, the air vent openings 160 enable air traveling distally through the fluid regulating safety tube 138 to be vented to atmosphere.

In one embodiment, the air embolism prevention assembly 112 and the elongated dispensing tube 108 may be incorporated into a single component, which may be referred to as a hollow tube or an applicator tip of a system for dispensing a flowable hemostat.

Figure 7:
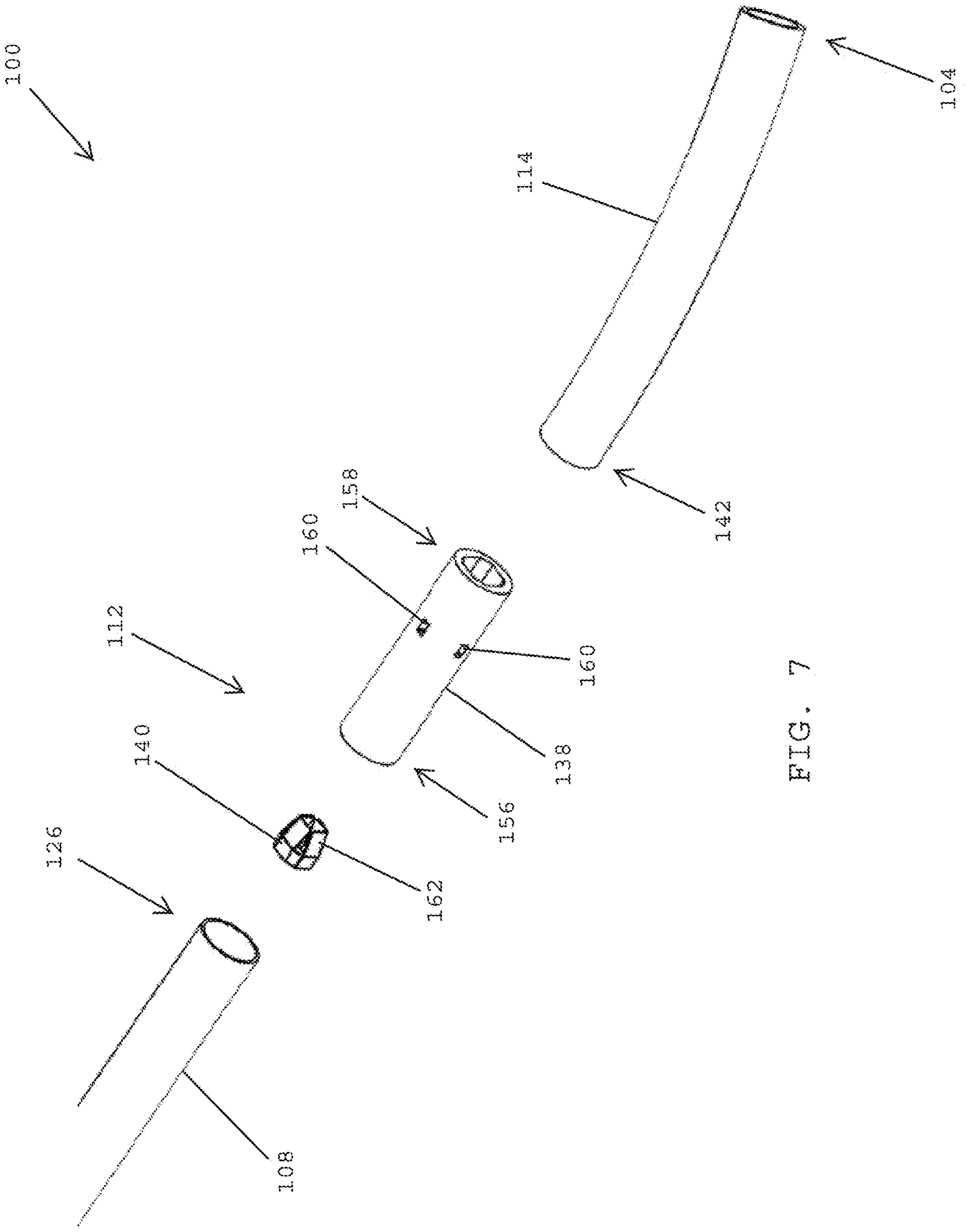
FIG. 7 is an exploded view of the distal end of the dispensing device shown in FIG. 6A including an air embolism prevention assembly having a fluid regulating safety tube and a valve.

Referring to FIG. 7, in one embodiment, the distal end 104 of the flowable hemostat dispensing device 100 preferably includes the air embolism prevention assembly 112 having the fluid regulating safety tube 138 with one or more air vent openings 160 and the valve 140 (i.e., flap valve) having one or more flexible flaps 160. In one embodiment, after the valve 140 is inserted into the elongated conduit of the fluid regulating safety tube 138, the proximal end 156 of the fluid regulating safety tube 138 is secured to the distal end 126 of the elongated dispensing tube 108 and the distal end 158 of the fluid regulating safety tube 138 is secured to the proximal end 142 of the dispensing tip 114.

Figure 8:
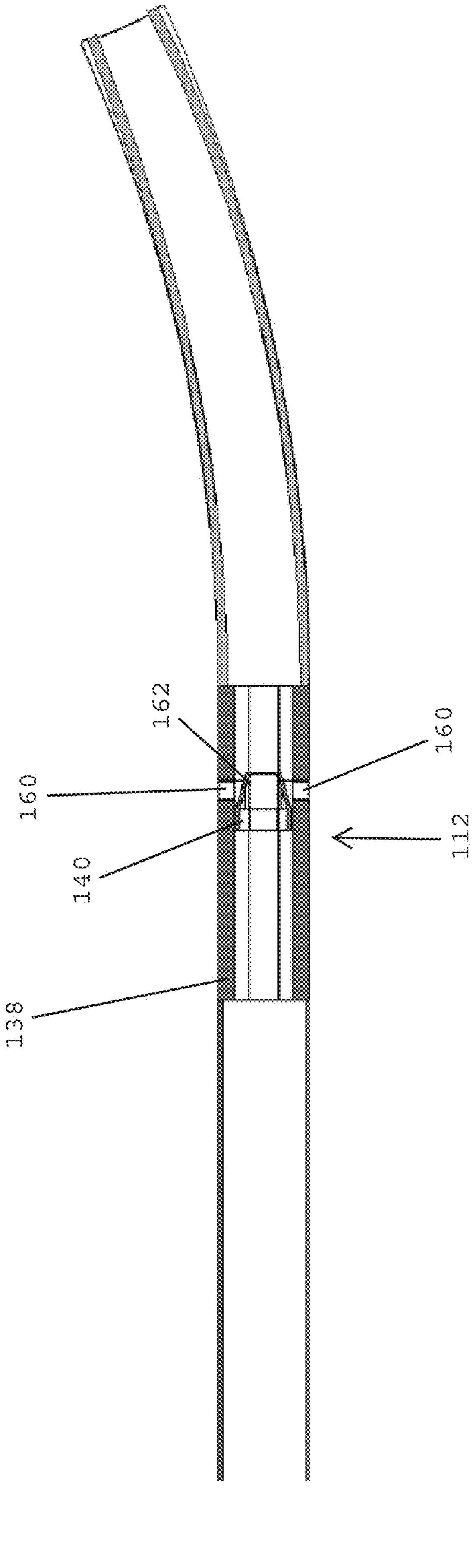
FIG. 8 is a cross-sectional view of the distal end of the dispensing device shown in FIG. 6A.

Referring to FIG. 8, in one embodiment, the valve 140 is preferably disposed inside the fluid regulating safety tube 138. The valve 140 preferably includes one or more hinged or flexible flaps 162 that are adapted to move between retracted and extended positions for selectively unsealing and sealing the air vent openings 160 that extend through the outer wall of the fluid regulating safety tube 138.

Figure 9A:
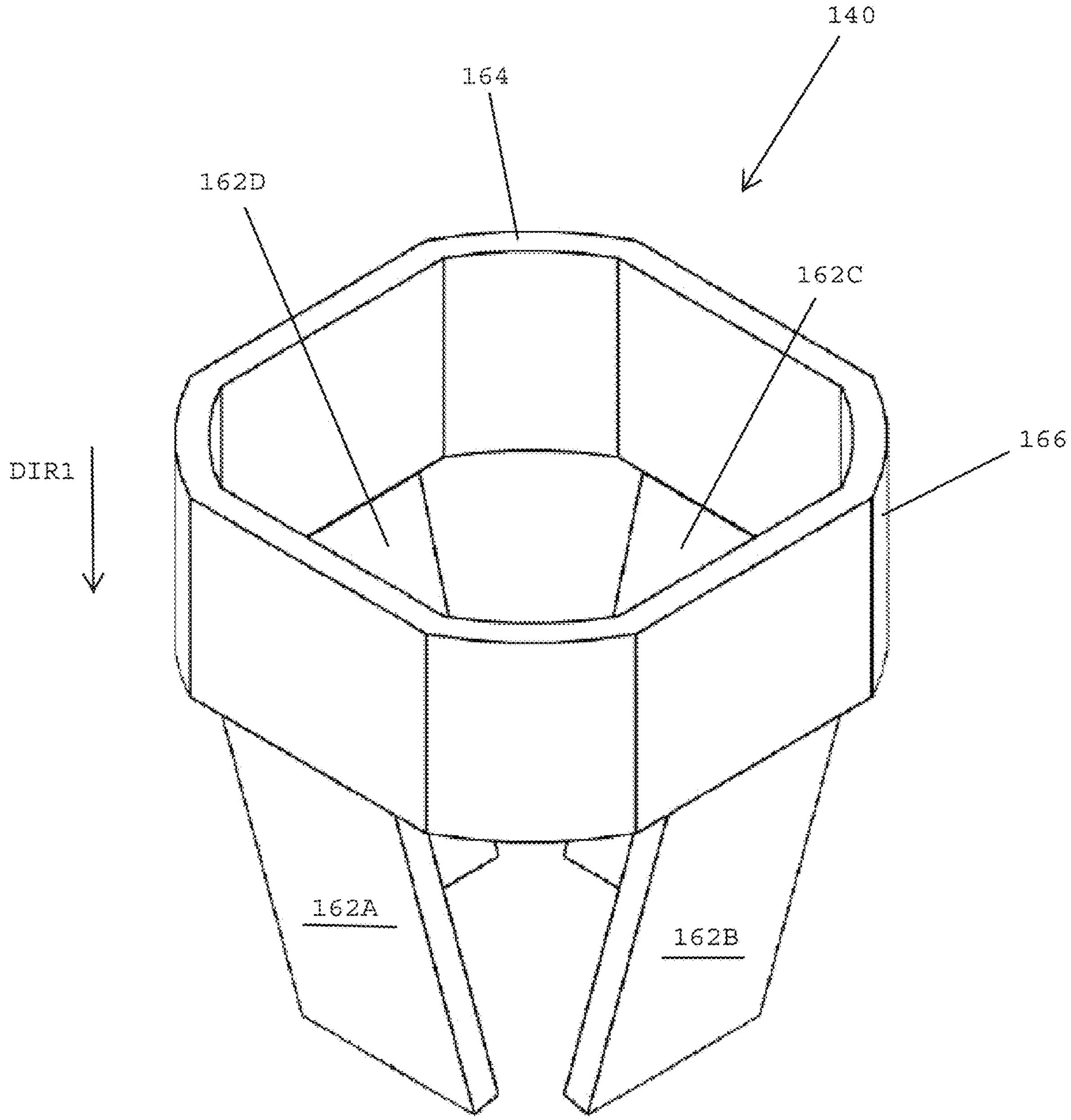
FIG. 9A is a perspective view of the valve shown in FIG. 7.
Figure 9B:
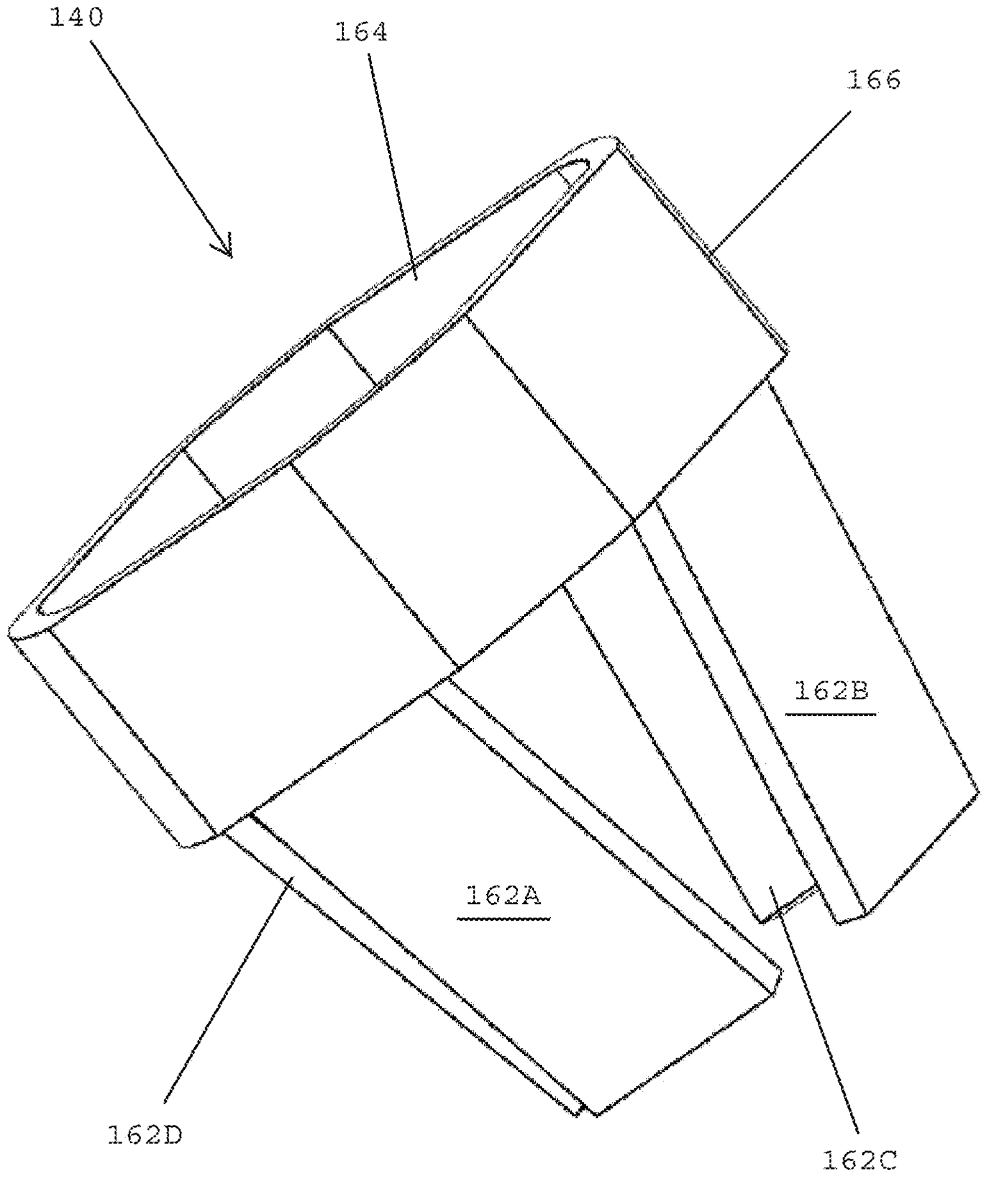
FIG. 9B is another perspective view of the valve shown in FIG. 9A.
Figure 9C:
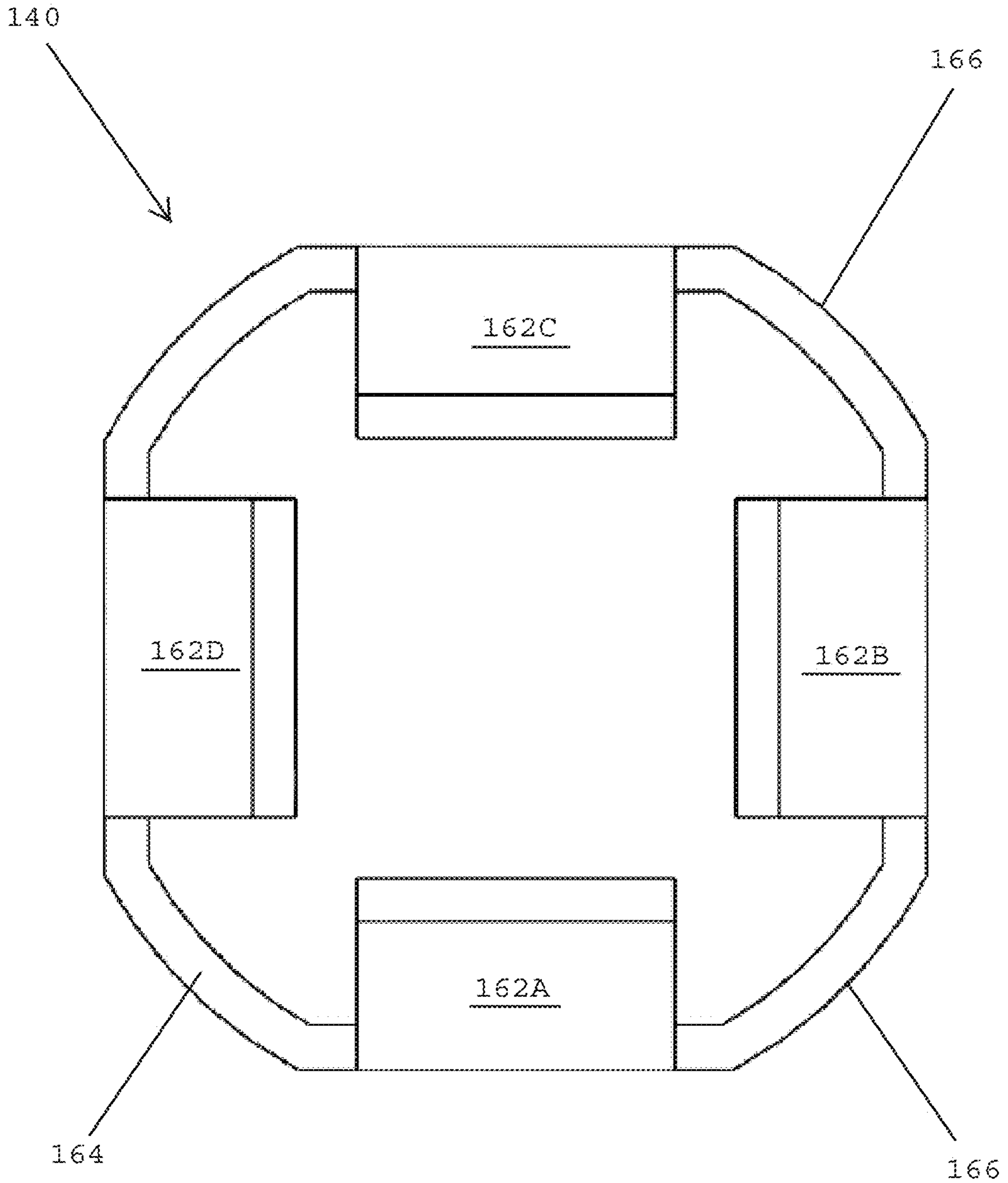
FIG. 9C is a distal end view of the valve shown in FIGS. 9A and 9B.

Referring to FIGS. 9A-9C, in one embodiment, the valve 140 (or flap valve) of the air embolism prevention assembly 112 (FIG. 8) preferably includes a plurality of flexible or hinged flaps 162A-162D, which have upper ends that are secured to a securing ring 164. In one embodiment, the securing ring 164 has an outer perimeter 166 that closely matches the inner diameter of the fluid regulating safety tube 138 (FIG. 8) so that a secure, stable connection may be formed between the valve 140 and the fluid regulating safety tube 138.

In one embodiment, the flexible flaps 162A-162D are normally biased into the retracted position that is shown in FIGS. 9A-9C. In one embodiment, when a flowable hemostat flows through the valve 140 in the distal direction DIR1 (FIG. 9A), the flowable hemostat material contacts the respective inner surfaces of the flexible flaps 162A-162D for forcing the flexible flaps to flex or move away from one another into an extended configuration, as will be described in more detail herein.

In one embodiment, the valve 140 may be made of a biocompatible material. In one embodiment, the valve 140 may be made of polymer materials or plastics. In one embodiment, the valve 140 may comprise PEPG.

In one embodiment, the flexible flaps of a valve may be separated from one another and not interconnected by a valve ring.

Figure 10:
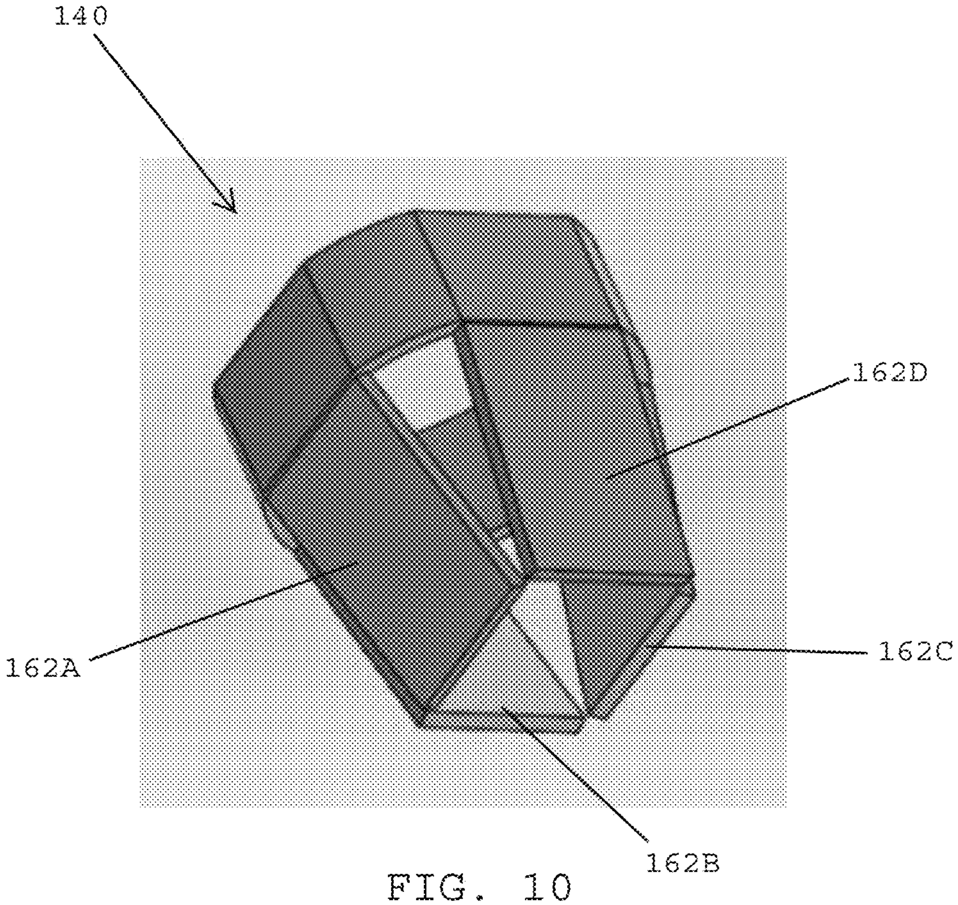
FIG. 10 is a perspective view of a valve of an air embolism prevention assembly, the valve having flexible flaps that are biased into a retracted position, in accordance with one embodiment of the present patent application.
Figure 11:
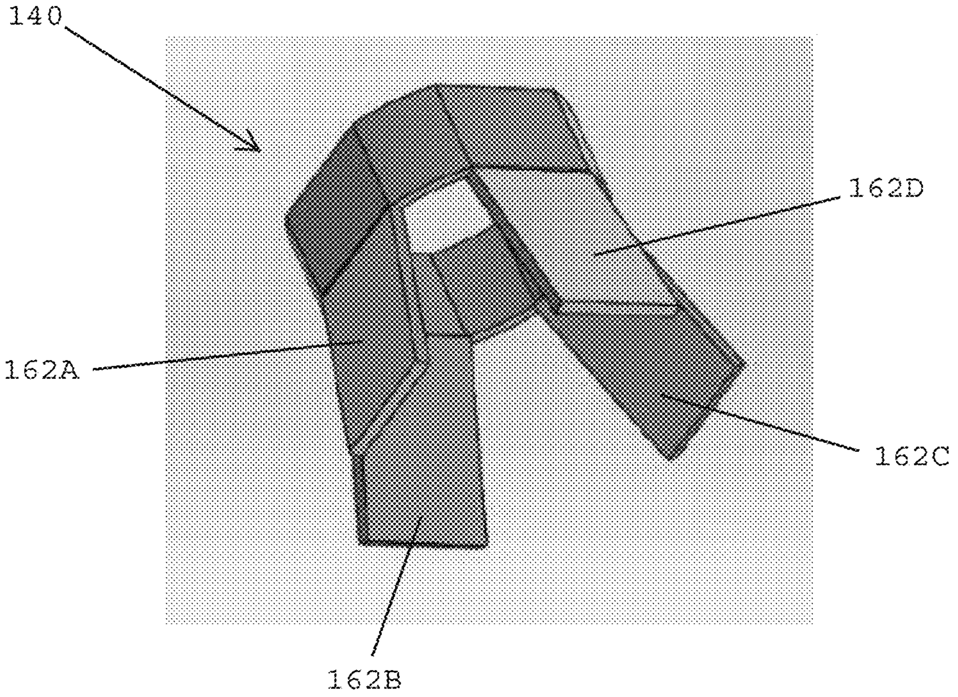
FIG. 11 is a perspective view of the valve of FIG. 10 with the flexible flaps in an extended position, in accordance with one embodiment of the present patent application.

Referring to FIGS. 10 and 11, in one embodiment, the flexible flaps 162A-162D of the valve 140 are preferably adapted to move between a retracted configuration (FIG. 10) and an extended configuration (FIG. 11). In one embodiment, the flexible flaps 162A-162D are normally biased into the retracted or open position (FIG. 10).

FIG. 10 shows the flexible flaps 162A-162D in the retracted position, whereupon the air vents of the fluid regulating safety tube are not sealed so that air may flow through the air vents.

FIG. 11 shows the flexible flaps 162A-162D in an extended position, whereupon the flexible flaps cover and/or seal the air vents of the fluid regulating safety tube for preventing air and/or the flowable hemostat material from flowing through the air vent openings of the fluid regulating safety tube.

Figure 12A:
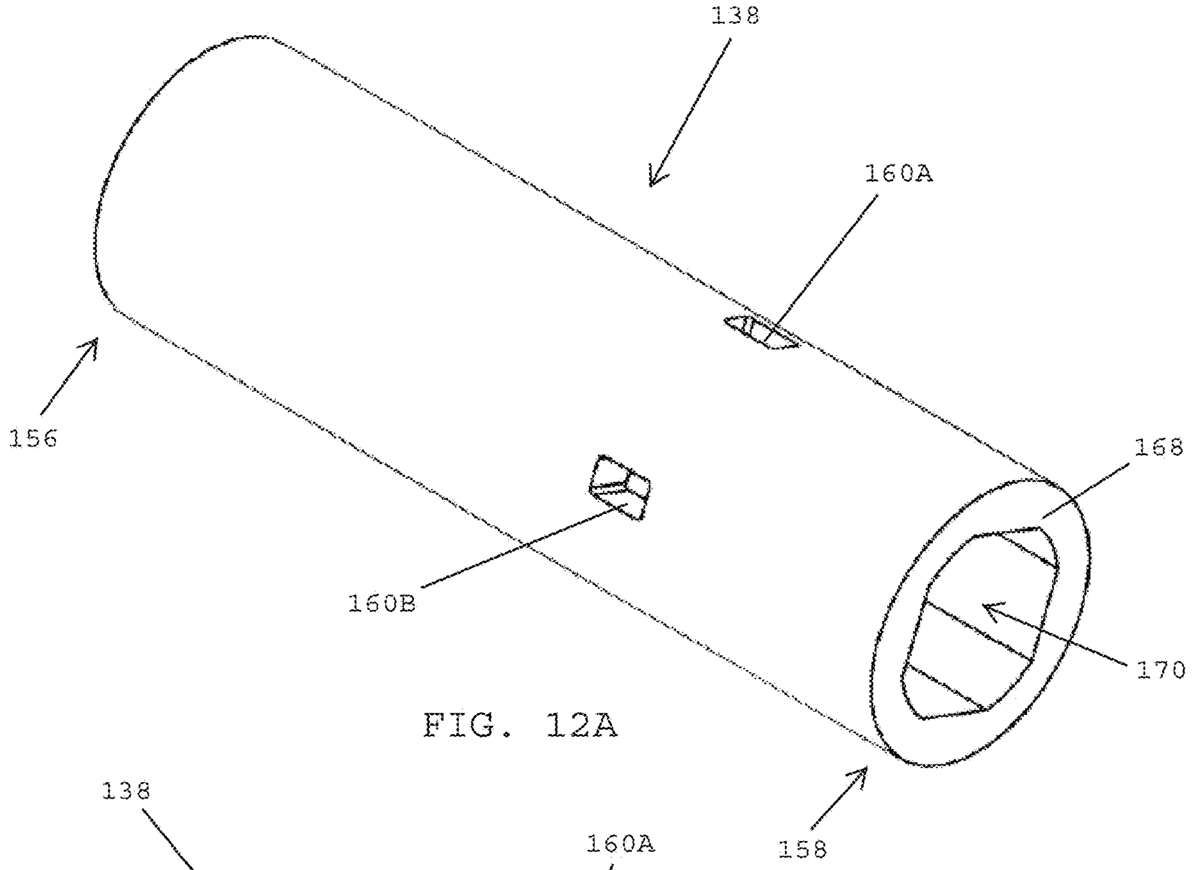
FIG. 12A is a perspective view of a fluid regulating safety tube of a flowable hemostat dispensing device, in accordance with one embodiment of the present patent application.
Figure 12B:
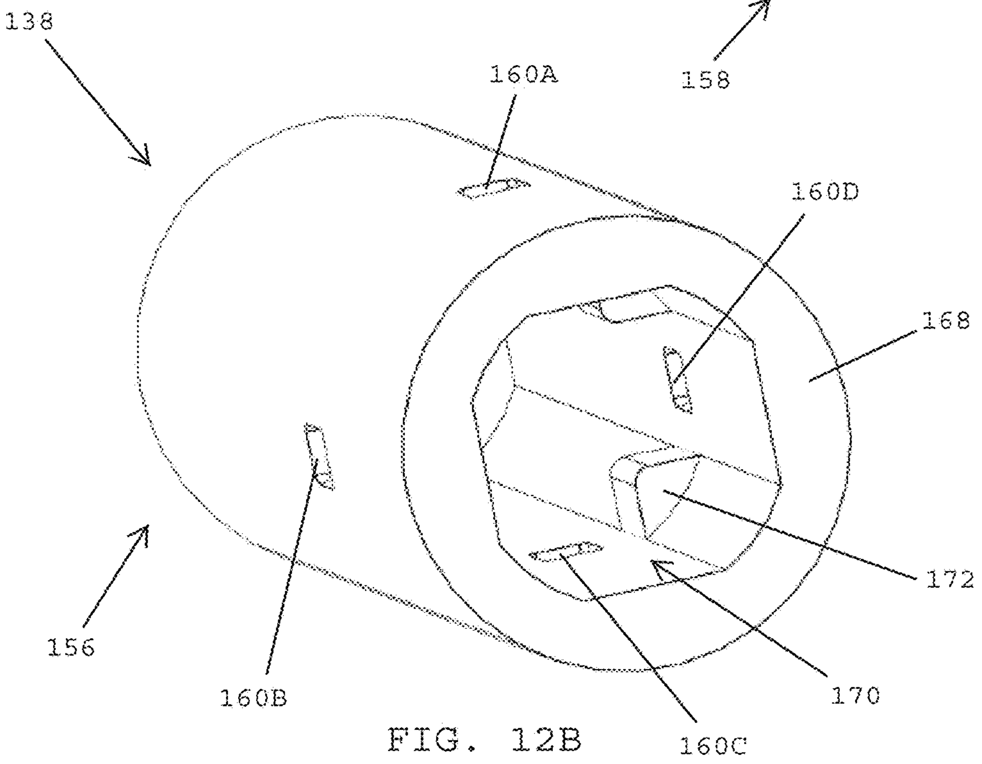
FIG. 12B is a perspective view of a distal end of the fluid regulating safety tube shown in FIG. 12A.

Referring to FIGS. 12A and 12B, in one embodiment, the fluid regulating safety tube 138 of the air embolism prevention assembly preferably has a tube-shaped outer wall 168 that extends from the proximal end 156 to the distal end 158 of the fluid regulating safety tube. The fluid regulating safety tube 138 preferably includes an elongated conduit 170 that extends along the length of the fluid regulating safety tube 138, from the proximal end 156 to the distal end 158 thereof. A flowable hemostat and/or air may flow through the elongated conduit 170 of the fluid regulating safety tube 138. In one embodiment, the fluid regulating safety tube 138 preferably includes a plurality of air vent openings 160A-160D that extend through the outer wall 168 so that air may be vented from the elongated conduit 170 to outside the fluid regulating safety tube 138.

Referring to FIG. 12B, in one embodiment, the fluid regulating safety tube 138 preferably includes one or more stops 172 that project inwardly from the inner surface of the outer wall 168 and into the elongated conduit 170 thereof. In one embodiment, when the valve 140 (FIG. 8) is inserted into the elongated conduit 170, a distal edge of the valve securing ring 164 (FIG. 9A) of the valve abuts against the proximal face of the stop 172 for insuring that the valve is held securely in place within the fluid regulating safety tube 138 and so that the flexible flaps 168A-168D (FIG. 9) are aligned with the air vent openings 160A-160D that extend through the outer wall 168 of the fluid regulating safety tube 138.

Figure 13:
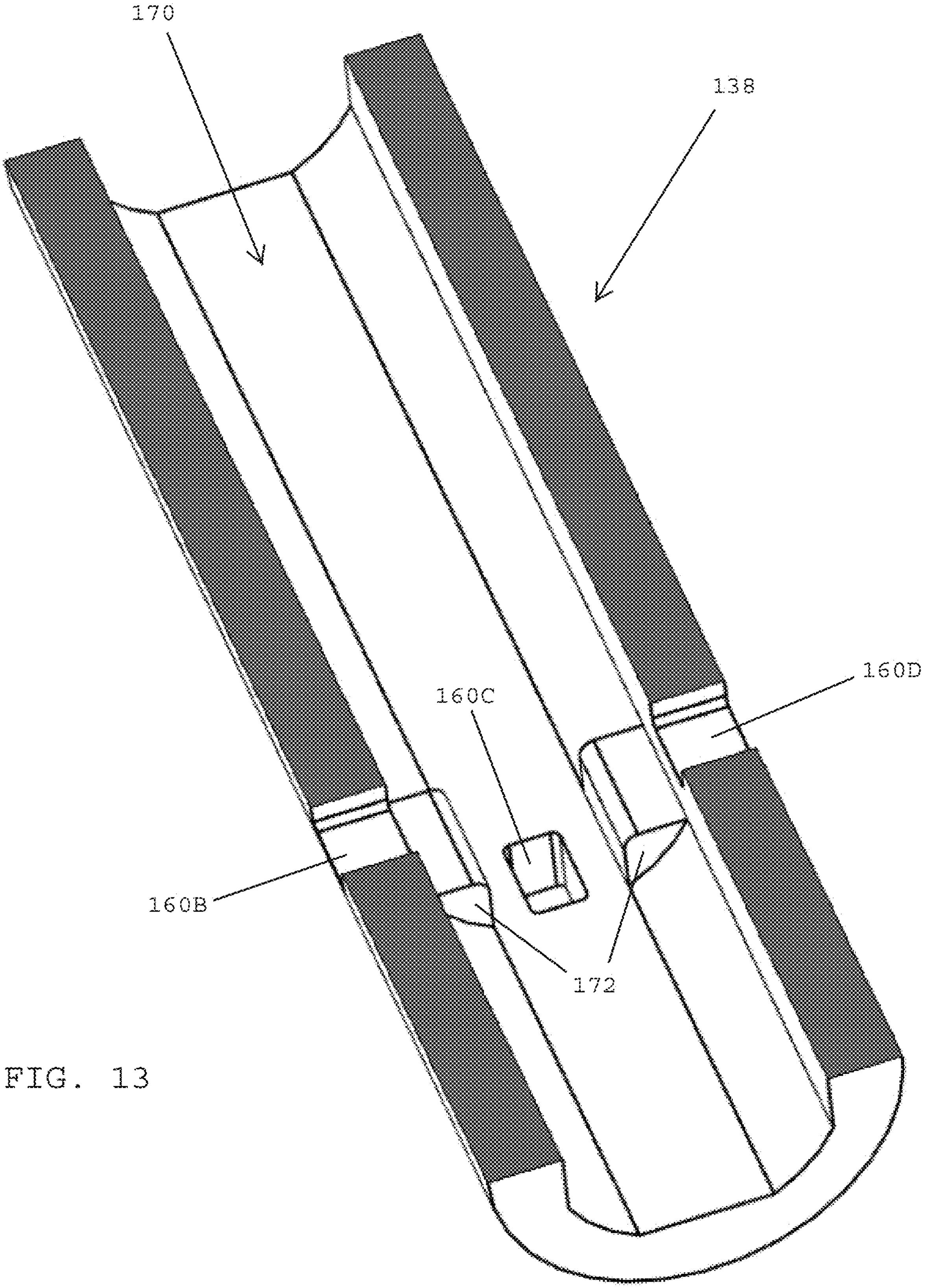
FIG. 13 is a cross-sectional view of the fluid regulating safety tube shown in FIGS. 12A and 12B.

Referring to FIG. 13, in one embodiment, the fluid regulating safety tube 138 preferably includes the one or more stops 172 that extend into the elongated conduit 170 of the fluid regulating safety tube 138. In one embodiment, the stops 172 are in general alignment with the air vent openings 160B-160D for ensuring that the flexible flaps of the valve 140 (FIG. 9A) are aligned with the air vent openings 106A-160C of the fluid regulating safety tube 138.

Figure 14:
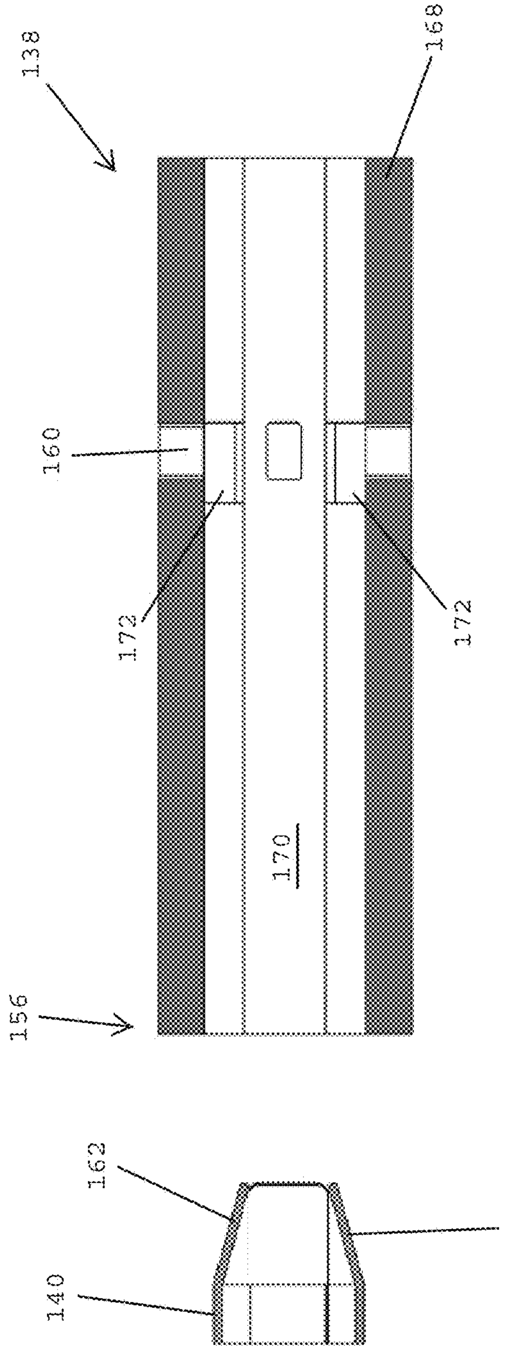
FIG. 14 is a cross-sectional view of an air embolism prevention assembly including a valve juxtaposed with a proximal end of a fluid regulating safety tube, in accordance with one embodiment of the present patent application.

Referring to FIG. 14, in one embodiment, the valve 140 may be assembled with the fluid regulating safety tube 138 by juxtaposing the flexible flaps 162 of the valve 140 with the proximal end 156 of the fluid regulating safety tube 138.

The stops 172 of the fluid regulating safety tube 138 desirably project into the elongated conduit 170 and may be aligned with the air vent openings 160 formed in the outer wall 168 of the fluid regulating safety tube 138.

Figure 15:
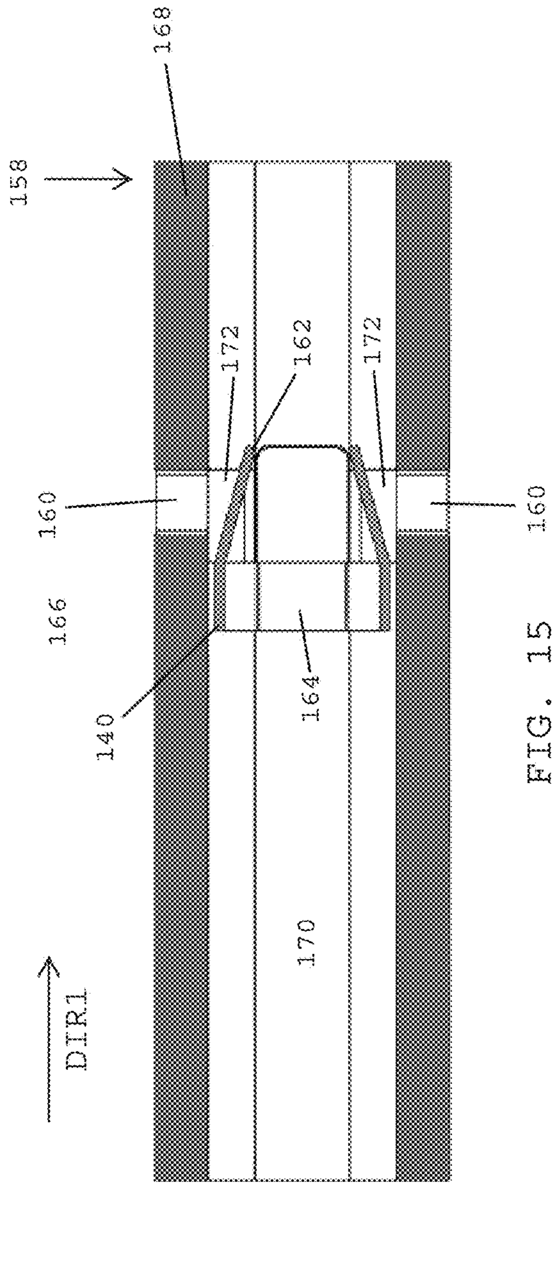
FIG. 15 shows the air embolism prevention assembly of FIG. 14 with the valve assembled with the fluid regulating safety tube, in accordance with one embodiment of the present patent application.

Referring to FIG. 15, in one embodiment, to assemble the valve 140 with the fluid regulating safety tube 138, the valve 140 may be advanced in the distal direction DIR1 through the elongated conduit 170 of the fluid regulating safety tube 138 until the distal edge of the valve ring 164 abuts against proximal faces of the respective stops 172. In one embodiment, the outer perimeter 166 of the valve ring 164 may engage (e.g., a friction fit) the inner surface of the outer wall 168 of the fluid regulating safety tube 138 for forming a secure attachment between the valve ring 164 and the fluid regulating safety tube 138, which may ensure proper alignment of the flexible flaps 162 with the air vent openings 160.

In one embodiment, after the valve 140 has been secured inside the fluid regulating safety tube 138, the flexible flaps 162 of the valve 140 are preferably aligned with the air vent openings 160 formed in the outer wall 168 of the fluid regulating safety tube 138.

As noted herein, the flexible flaps 162 of the valve 140 are normally biased into the retracted position shown in FIG. 15, whereupon the air vent openings 160 are not sealed by the flexible flaps 162. In one embodiment, as flowable hemostat material is directed in the distal direction DIR1 through the elongated conduit 170 of the fluid regulating safety tube 138, the flowable material impinges upon the flexible flaps 162 for forcing the flaps to move away from one another and into an extended position (FIG. 11) for covering and/or sealing the air vent openings 160, thereby preventing any flowable hemostat material and/or air from passing through the air vent openings 160. As a result, the flowable hemostat material will pass over the air vent openings 160 for being directed toward the distal end 168 of the fluid regulating safety tube 138.

Figure 16A:
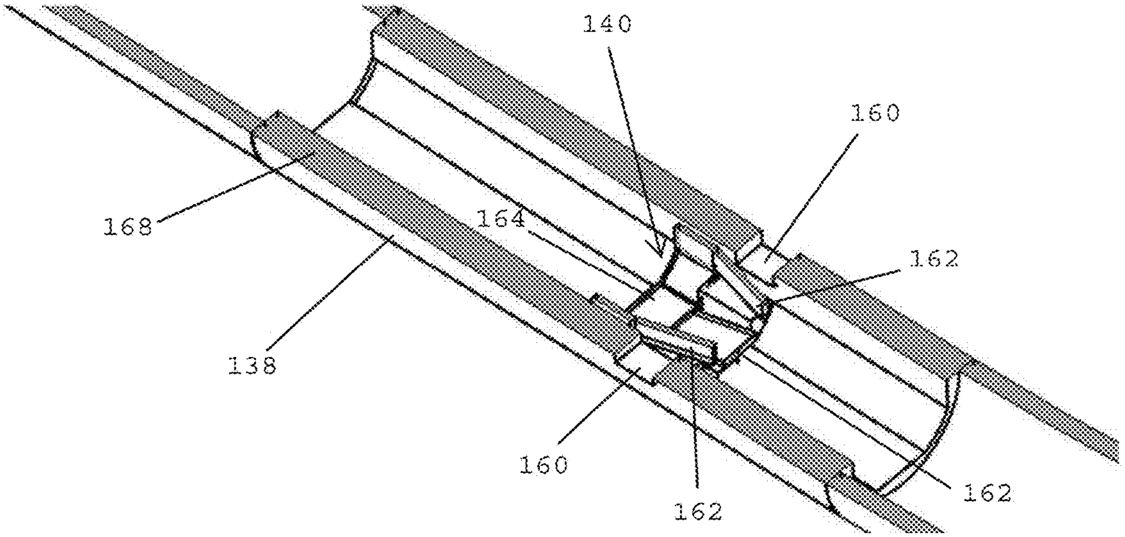
FIG. 16A is a perspective, cross-sectional view of an air embolism prevention assembly including a valve and a fluid regulating safety tube, in accordance with one embodiment of the present application.
Figure 16B:
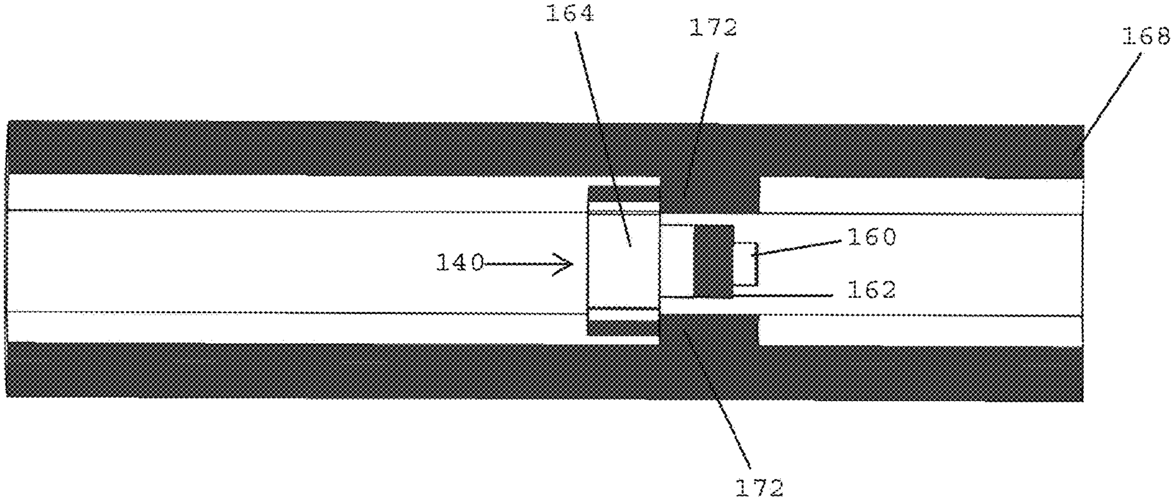
FIG. 16B is another cross-sectional view of the air embolism prevention assembly shown in FIG. 16A.

Referring to FIGS. 16A and 16B, in one embodiment, after the valve 140 has been assembled with the fluid regulating safety tube 138 to form the air embolism prevention assembly 112, a distal edge of the valve ring 164 abuts against proximal faces of the stops 172 for aligning the flexible flaps 162 of the valve 140 with the air vent openings 160 formed in the outer wall 168 of the fluid regulating safety tube 138.

Figure 17A:
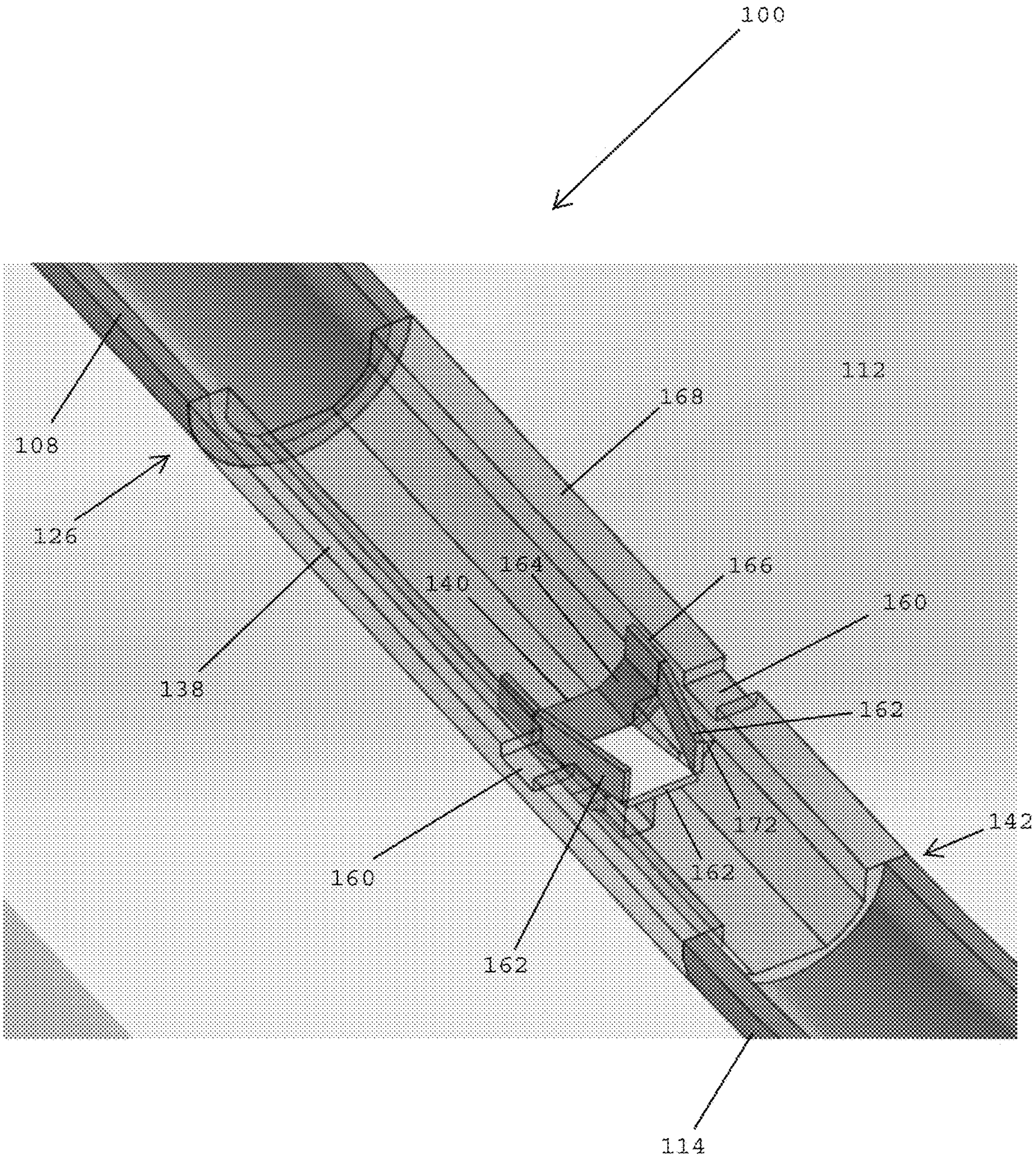
FIG. 17A illustrates a first stage of a method of directing a flowable hemostat through an air embolism prevention assembly of a flowable hemostat dispensing device, in accordance with one embodiment of the present patent application.

Referring to FIG. 17A, in one embodiment, a system including dispensing device 100 for dispensing a flowable hemostat to control bleeding preferably includes an air embolism prevention assembly 112 that is located between a distal end 126 of an elongated dispensing tube 108 and a proximal end 142 of a dispensing tip 114. In one embodiment, the air embolism prevention assembly 112 preferably includes the fluid regulating safety tube 138 having the outer wall 168 with air vents 160 passing therethrough. The valve 140 is assembled inside the fluid regulating safety tube 138 and is held in place by the stops 172. The valve may also be held in place by engagement of the outer perimeter 166 of the valve ring 164 with the inner surface of the outer wall 168 of the fluid regulating safety tube 138. In FIG. 17A, the flexible flaps 162 are preferably biased in a retracted position so that the air vents 160 are not sealed by the flexible flaps 162.

Figure 17B:
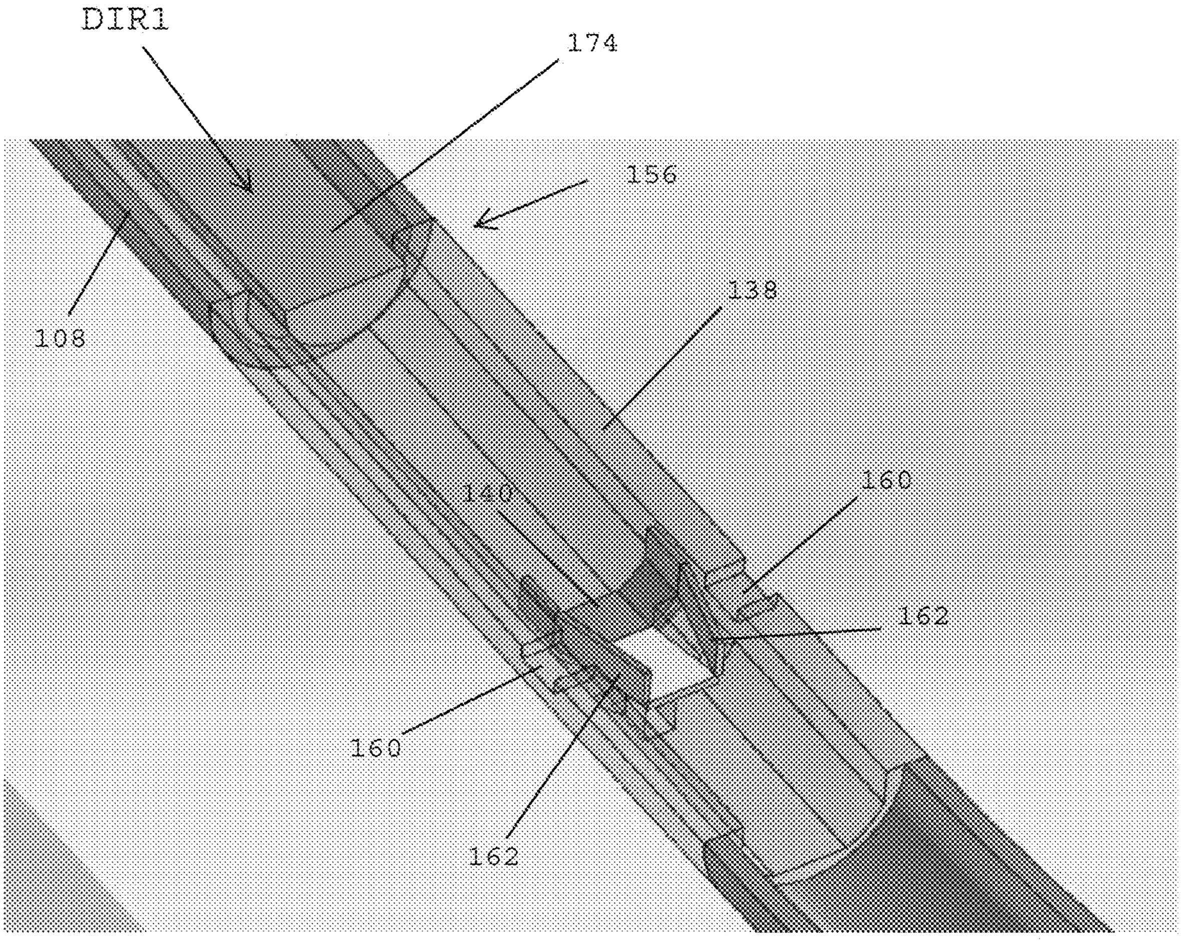
FIG. 17B illustrates a second stage of a method of directing a flowable hemostat through an air embolism prevention assembly of a flowable hemostat dispensing device, in accordance with one embodiment of the present patent application.

Referring to FIG. 17B, in one embodiment, depressing the syringe plunger in the distal direction DIR1 (FIG. 2) forces the flowable hemostat material 174 to flow distally through the elongated dispensing tube 108. In one embodiment, the flowable hemostat material 174 flows distally through the elongated conduit of the elongated dispensing tube 108 until it reaches the proximal end 156 of the fluid regulating safety tube 138. At the dispensing stage shown in FIG. 17B, the flowable hemostat 174 has not yet contacted the flexible flaps 162 of the valve 140 so that the flexible flaps 162 remain biased in their normal retracted position in which the air vent openings 160 of the fluid regulating safety tube 138 are not sealed by the flexible flaps 162.

Figure 17C:
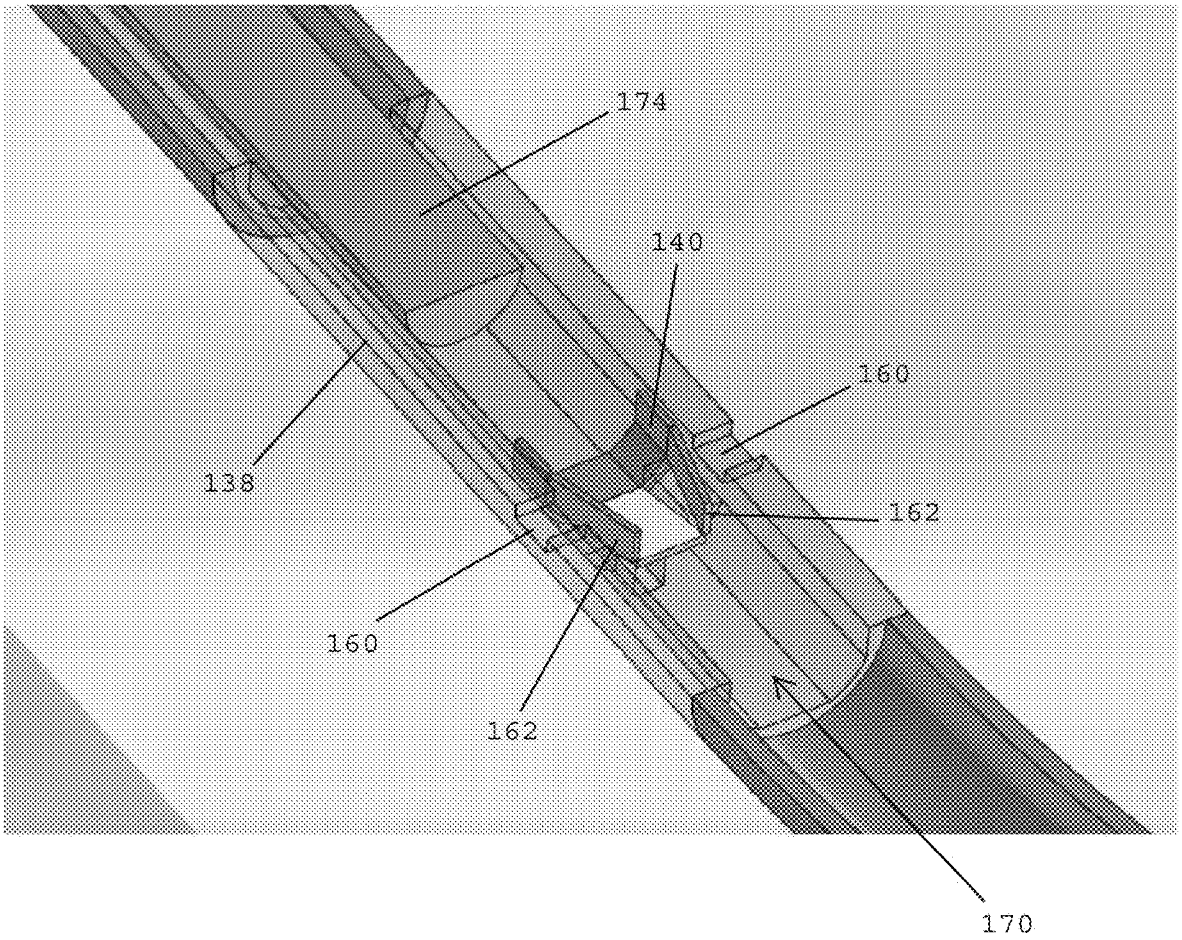
FIG. 17C illustrates a third stage of a method of dispensing a flowable hemostat through an air embolism prevention assembly of a flowable hemostat dispensing device, in accordance with one embodiment of the present patent application.

Referring to FIG. 17C, in one embodiment, the flowable hemostat material 174 flows distally into the elongated conduit 170 of the fluid regulating safety tube 138 for being directed toward the valve 140 secured inside the fluid regulating safety tube 138. The flexible flaps 162 remain in the retracted configuration so that the air vent openings 160 formed in the fluid regulating safety tube remain open and unsealed.

Figure 17D:
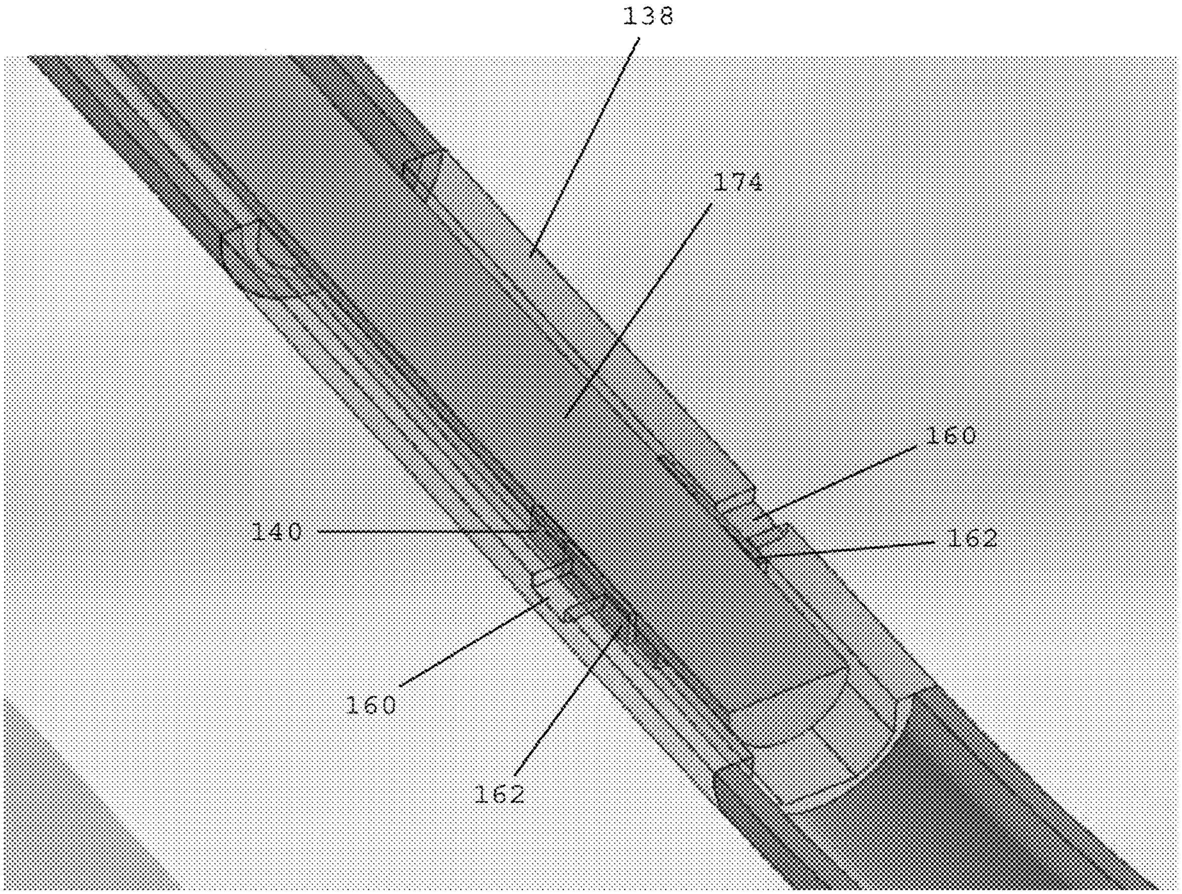
FIG. 17D illustrates a fourth stage of a method of directing a flowable hemostat through an air embolism prevention assembly of a flowable hemostat dispensing device, in accordance with one embodiment of the present patent application.

Referring to FIG. 17D, in one embodiment, when the flowable hemostat material 174 flows through the valve 140, the flowable material contacts the flexible flaps 162 of the valve, which forces the flexible flaps to move into the extended position for sealing the air vent openings 160 of the fluid regulating safety tube 138.

Figure 17E:
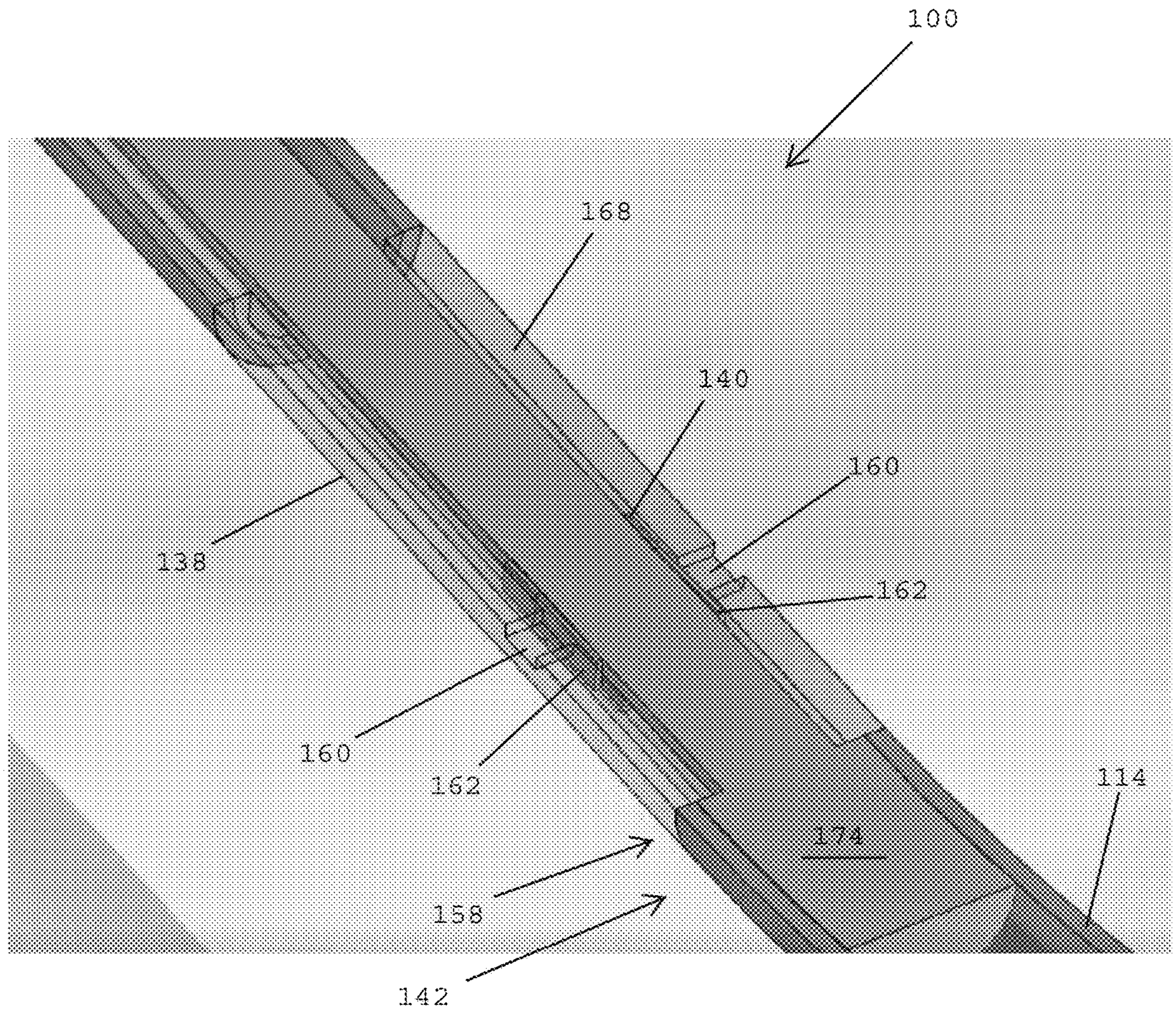
FIG. 17E illustrates a fifth stage of a method of directing a flowable hemostat through an air embolism prevention assembly of a flowable hemostat dispensing device, in accordance with one embodiment of the present patent application.

Referring to FIG. 17E, in one embodiment, the flowable hemostat material 174 preferably flows beyond the distal end 158 of the fluid regulating safety tube 138 and into the opening at the proximal end 142 of the dispensing tip 114 for being dispensed from the distal end 104 (FIG. 1) of the dispensing device 100. As the flowable hemostat material 174 flows through the valve 140, the flowable hemostat material engages the flexible flaps 162 for forcing the flexible flaps to move into the extended position for sealing the air vent openings 160 of the fluid regulating safety tube 138.

Figure 17F:
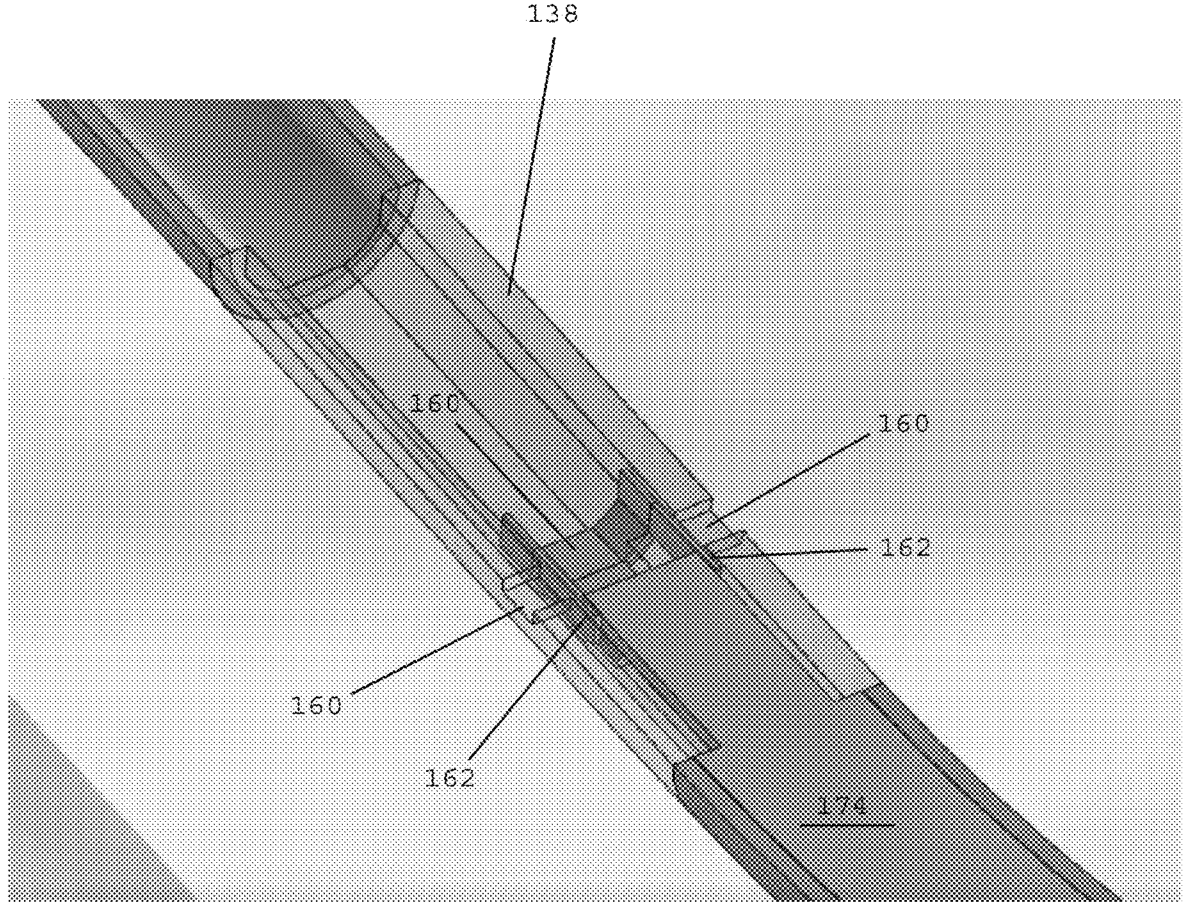
FIG. 17F illustrates a sixth stage of a method of directing a flowable hemostat through an air embolism prevention assembly of a flowable hemostat dispensing device, in accordance with one embodiment of the present patent application.

Referring to FIG. 17F, in one embodiment, while the flowable hemostat 174 passing through the fluid regulating safety tube 138 remains in contact with the flexible flaps 162 of the valve 140, the hemostat material will force the flexible flaps 162 to remain in the extended position for sealing the air vent openings 160 of the fluid regulating safety tube 138.

Figure 17G:
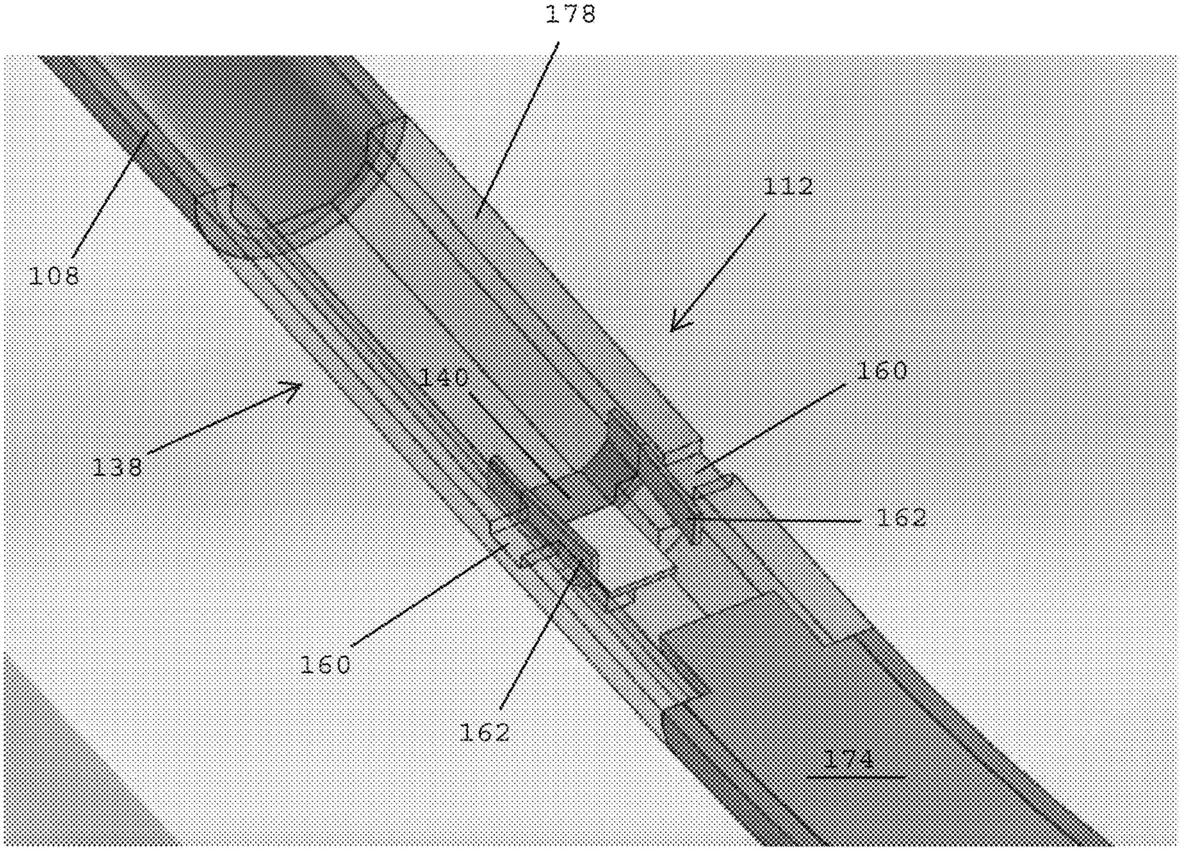
FIG. 17G illustrates a seventh stage of a method of directing a flowable hemostat through an air embolism prevention assembly of a flowable hemostat dispensing device, in accordance with one embodiment of the present patent application.

Referring to FIG. 17G, in one embodiment, once the flowable hemostat material 174 has traveled beyond the valve 140, the flowable hemostat is no longer in contact with flexible flaps 162 of the valve, whereupon the flexible flaps are free to move back (e.g., spring back) to the normal retracted position (i.e., the open position). In the retracted position, the air vent openings 160 are unsealed and/or opened.

In prior art devices, the residual flowable hemostat 174 that remains inside the distal end of the dispensing device is often not used and is deemed to be a sacrificial quantity of flowable hemostat. In prior art devices, the residual flowable hemostat that remains within the distal end of the dispensing tip is simply not used and is thrown away. This is not cost effective and wastes valuable resources. In some instances, up to 40% of the flowable hemostat that is loaded into a syringe is not used. For example, for 8 ml of flowable hemostat that is prepared, up to 3 ml or more may not be dispensed and go to waste. In some instances, the surgeon may detach the proximal end of the elongated tube 108 from the syringe connector and use a stylus or stick to expel or push the residual flowable hemostat from the distal end of the dispensing device. Detaching the elongated tube from the syringe connector wastes valuable time during a surgical procedure and forces the surgeon to remove his or her eyes from monitoring the surgical procedure, which could create safety or efficiency issues.

The present patent application discloses improved systems, devices, and methods of safely and efficiently expelling a residual flowable hemostat from a distal end of a dispensing device, without requiring the proximal end of the dispensing tube to be detached from a syringe connector and/or a syringe barrel, and without forcing a surgeon to remove his or her eyes from the surgical site.

Figure 18:
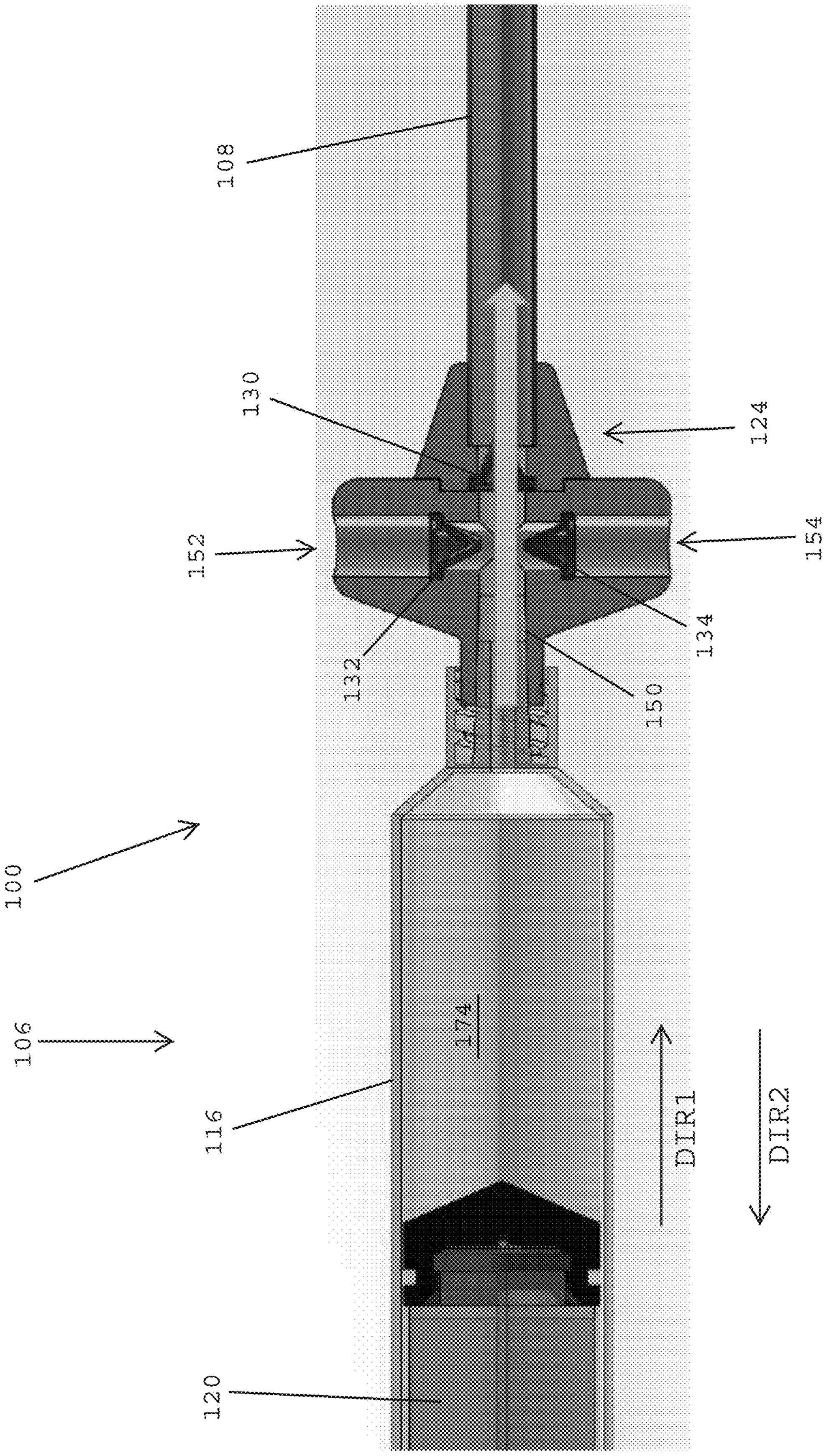
FIG. 18 illustrates a method of directing a flowable hemostat through a syringe connector having a one-way fluid valve, in accordance with one embodiment of the present patent application.
Figure 19:
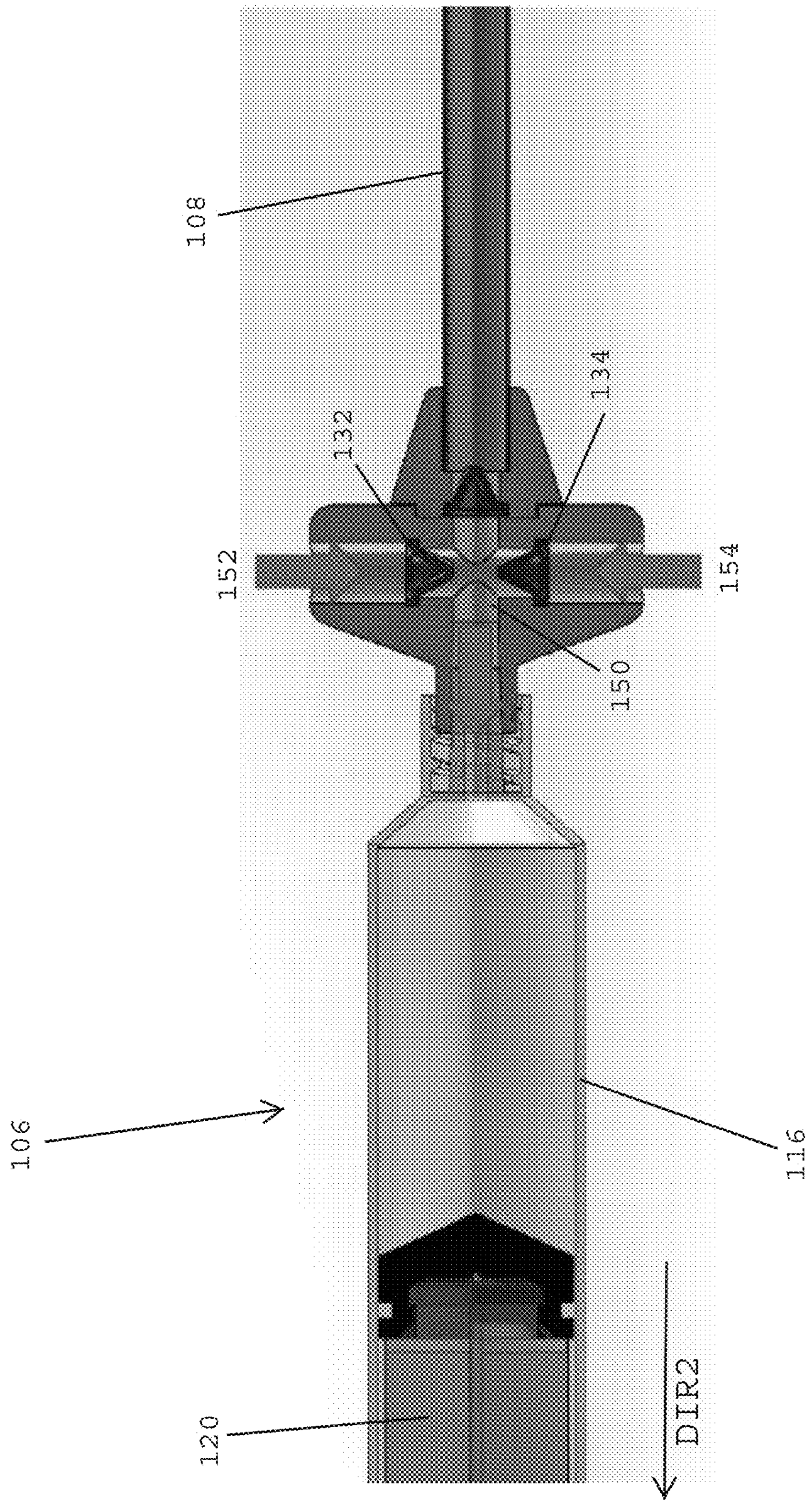
FIG. 19 illustrates a method of drawing air into the syringe connector of FIG. 18, the syringe connector having first and second one-way air valves, in accordance with one embodiment of the present patent application.
Figure 20:
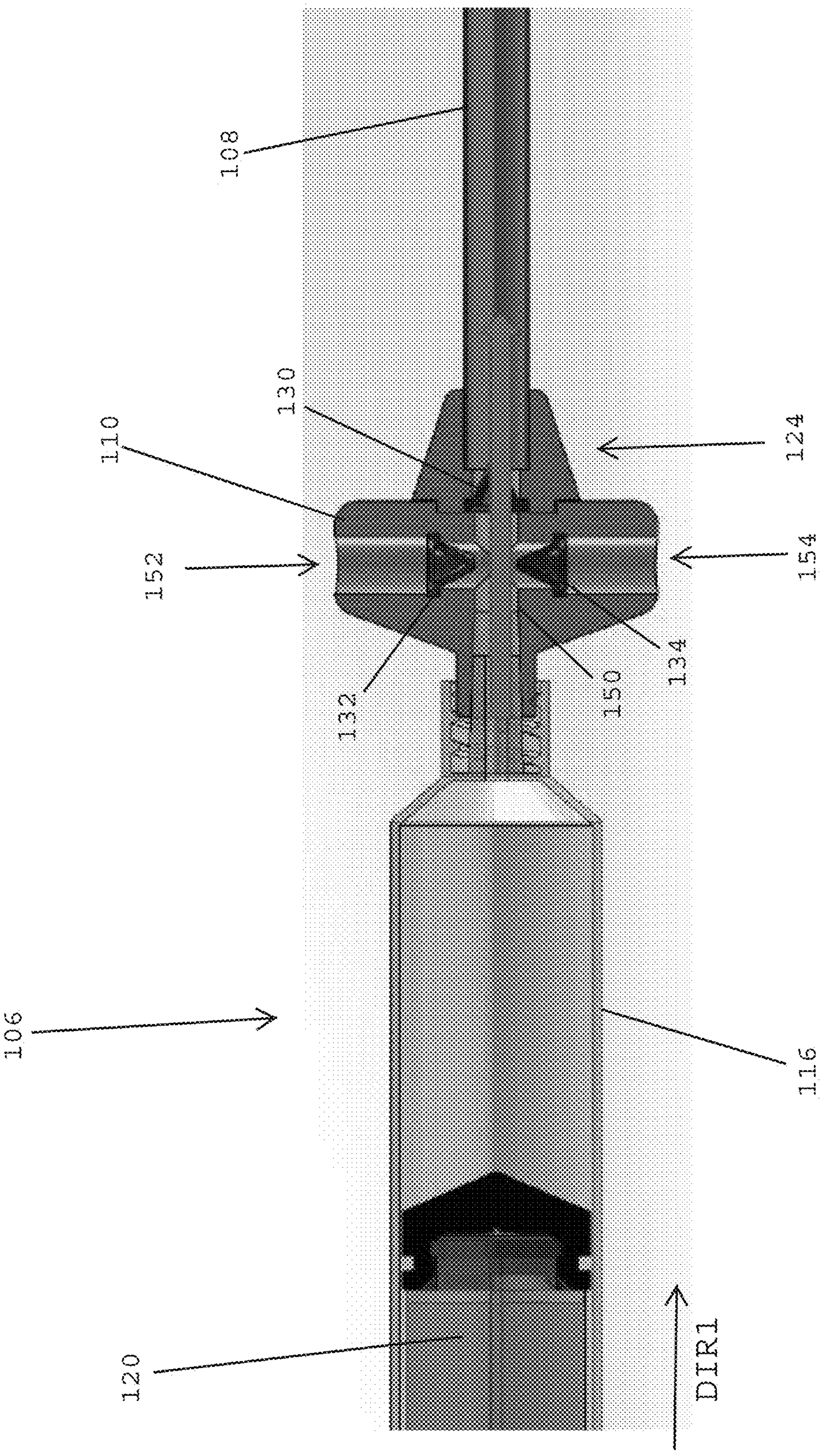
FIG. 20 illustrates a method of directing air through the one-way fluid valve of the syringe connector shown in FIGS. 18 and 19, in accordance with one embodiment of the present patent application.

FIGS. 18-20 show the operation of the one-way valves that are disposed within the syringe connector 110 of the flowable hemostat dispensing device 100 shown and described herein. The one-way valves enable the residual flowable hemostats that remain within the distal ends of applicator tips to be safely and efficiently expelled from and/or pushed out of the distal ends of applicator tips of dispensing devices. Referring to FIG. 18, in one embodiment, when the syringe plunger 120 of the syringe 116 is depressed in the distal direction DIR1, the flowable hemostat material 174 contained within the syringe barrel 116 is forced to flow through the fluid conduit 150 of the syringe connector, through the one-way fluid valve 130 and into the proximal end 124 of the elongated dispensing tube 108. The one-way fluid valve 130 does not allow the flowable hemostat to back up and flow in the proximal direction DIR2. The first and second one-way air valves 132, 134 remain closed as the flowable hemostat material 174 flows through the syringe connector 110 to prevent any of the flowable hemostat material from escaping via the first and second air inlet openings 152, 154 of the syringe connector 110.

Referring to FIG. 19, in one embodiment, after the flowable hemostat material has been fully expelled from the syringe barrel 116 of the syringe 106, the syringe plunger 120 may be retracted in the proximal direction DIR2 for drawing air into the first and second air inlets 152, 154 of the syringe connector 110, whereupon the air passes through the first and second one-way air valves 132, 134 for being drawn into the syringe barrel 116 of the syringe 106. As the air is drawn through the first and second air inlet openings 152, 154, the one-way fluid valve 130 disposed within the central fluid conduit 150 remains closed for preventing any of the flowable hemostat material present in the elongated dispensing tube 108 from being drawn back into the syringe barrel 116 of the syringe 106.

Referring to FIG. 20, in one embodiment, after air has been drawn into the syringe barrel 116 of the syringe 106, the syringe plunger 120 may again be depressed in the distal direction DIR1 for forcing the air within the syringe barrel 116 into the fluid conduit 150 of the syringe connector 110, whereupon the air passes through the one-way fluid valve 130 and into the proximal end 124 of the elongated dispensing tube 108. In FIG. 20, the one-way fluid valve 130 is open for allowing the air to pass therethrough, while the first and second one-way air valves 132, 134 remain closed for preventing any of the air from escaping laterally from the syringe connector 110 via the first and second inlet openings 152, 154.

The air that is forced into the elongated dispensing tube will travel to the distal end of the dispensing device to force and/or push out the residual flowable hemostat from the distal end of the dispending device. Referring to FIGS. 17G and 20, during this stage of pushing out the residual flowable hemostat from the distal end of the dispensing device, the flexible flaps 162 of the valve 140 (FIG. 17G) of the air embolism prevention assembly are unsealed from the air vents 160 to enable the air to escape through the outer wall of the fluid regulating safety tube 138, which prevents the air from leaving the distal end of the dispensing device for preventing air embolisms.

Figure 21:
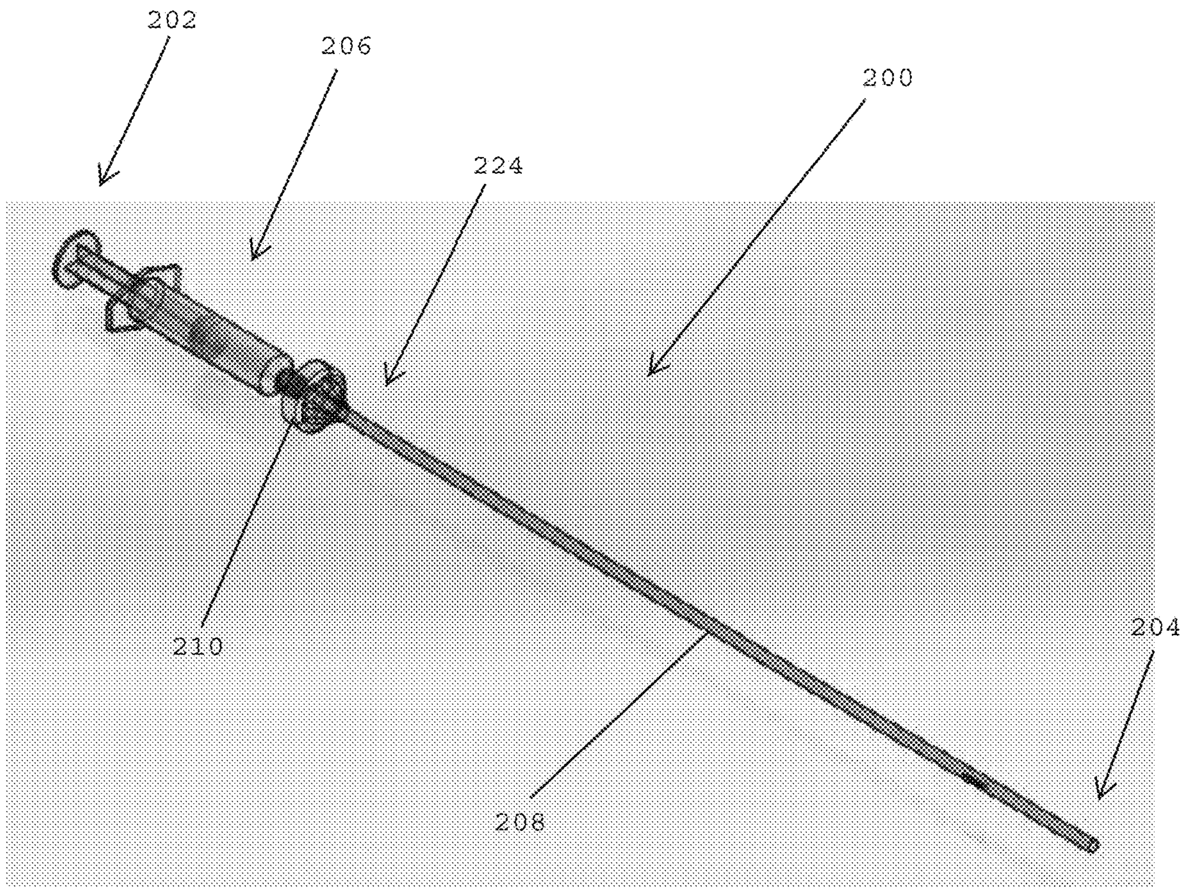
FIG. 21 is a perspective view of a system including a dispensing device for dispensing a flowable hemostat, the dispensing device including an elongated dispensing tube having an air embolism prevention assembly, in accordance with one embodiment of the present patent application.

Referring to FIG. 21, in one embodiment, a dispensing device 200 for a flowable hemostat preferably has a proximal end 202 and a distal end 204. In one embodiment, the flowable hemostat dispensing device 200 preferably includes a syringe 206 that contains a flowable hemostat material, an elongated dispensing tube 208 (i.e., a hollow tube), and a syringe connector 210 that interconnects a distal end of the syringe 206 with a proximal end 224 of the elongated dispensing tube 208.

Figure 22A:
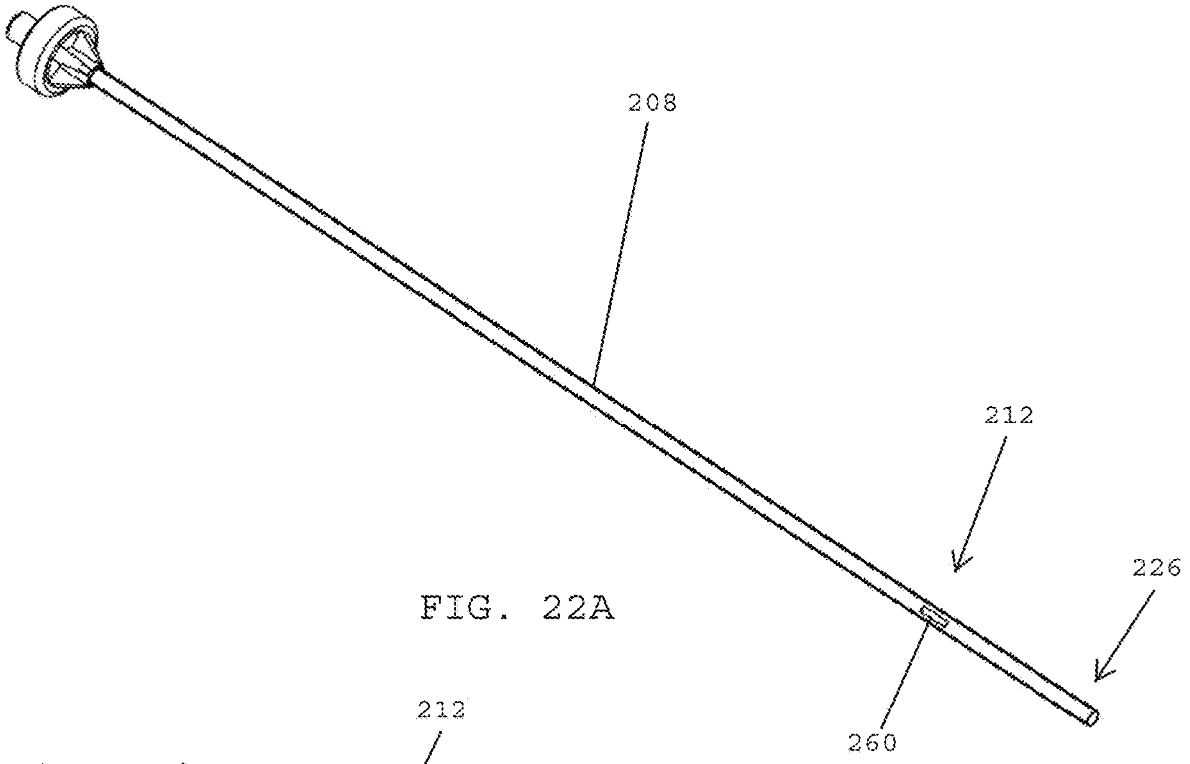
FIG. 22A is a perspective view of the elongated dispensing tube shown in FIG. 21 with an air embolism prevention assembly incorporated into the elongated dispensing tube, in accordance with one embodiment of the present patent application.
Figure 22B:
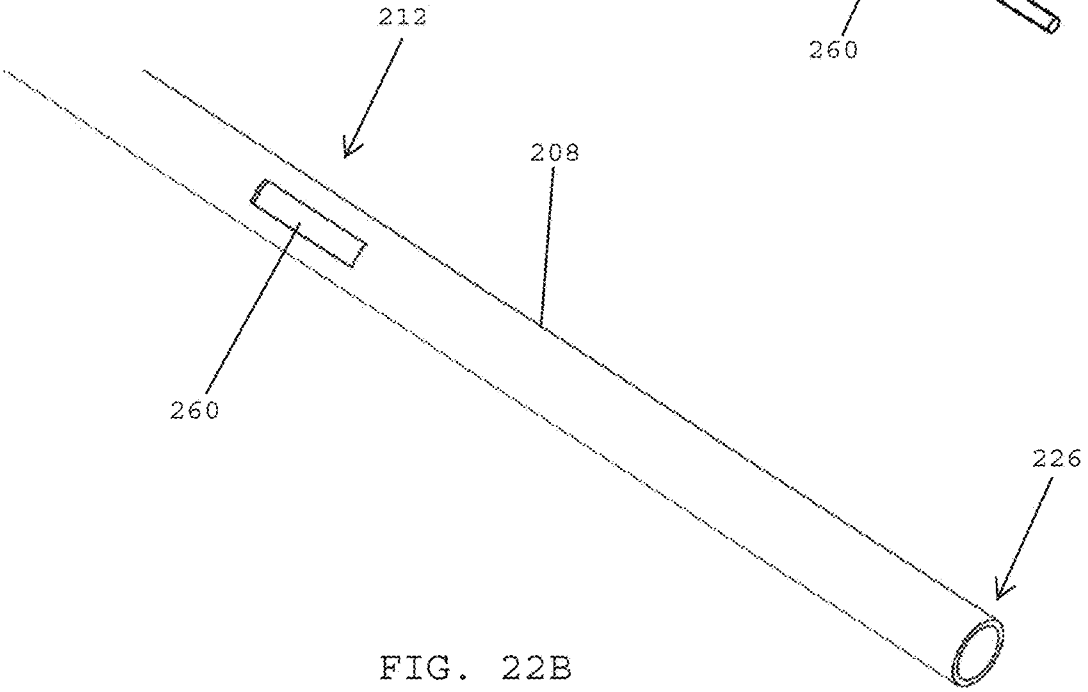
FIG. 22B is a magnified view of the distal end of the elongated dispensing tube and the air embolism prevention assembly shown in FIG. 22A.

Referring to FIGS. 22A and 22B, in one embodiment, the elongated dispensing tube 208 preferably has a distal end 226 that is adapted to dispense a flowable hemostat material.

The elongated dispensing tube 208 preferably has an air embolism prevention assembly 212 including an air vent 260 that is formed in an outer wall of the elongated dispensing tube 208.

Figure 23:
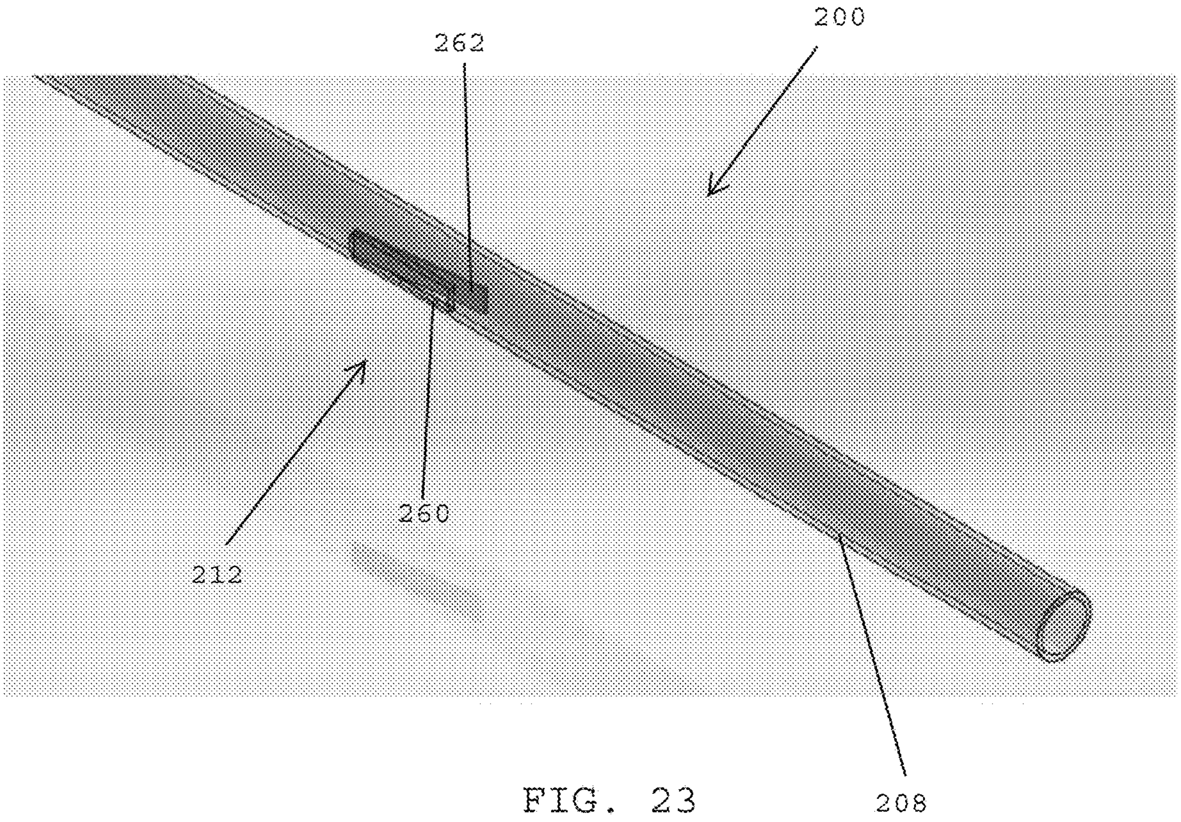
FIG. 23 is a magnified view of a distal end of a flowable hemostat dispensing device including an air embolism prevention assembly having a flexible flap, in accordance with one embodiment of the present patent application.
Figure 24:
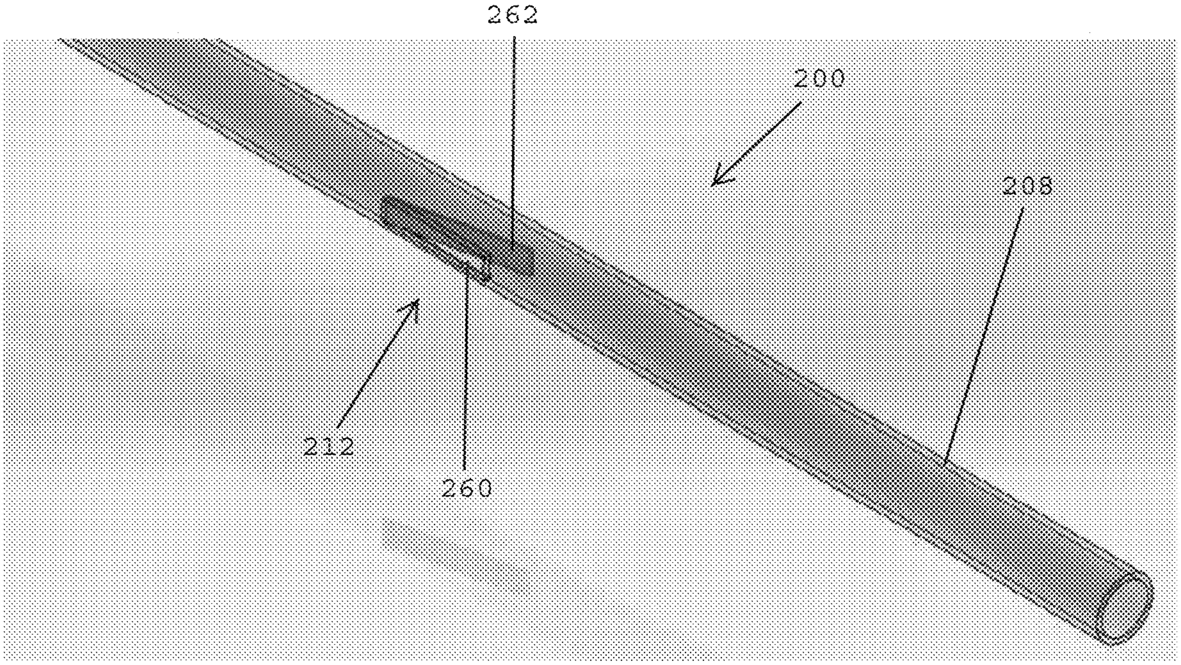
FIG. 24 shows the flexible flap of the air embolism prevention assembly of FIG. 23 in an open position.

Referring to FIGS. 23 and 24, in one embodiment, the flowable hemostat dispensing device 200 preferably includes the air embolism prevention assembly 212 having the air vent opening 260 that is formed in the outer wall of the elongated dispensing tube 208. In one embodiment, the air embolism prevention assembly 212 preferably includes a flexible flap 262 that is normally biased into a retracted position (i.e., an open position) in which the flexible flap 262 does not cover and/or seal the air vent 260 formed in the outer wall of the elongated dispensing tube 208. When the air vent is unsealed, air may pass through the opening of the air vent.

Figure 25A:
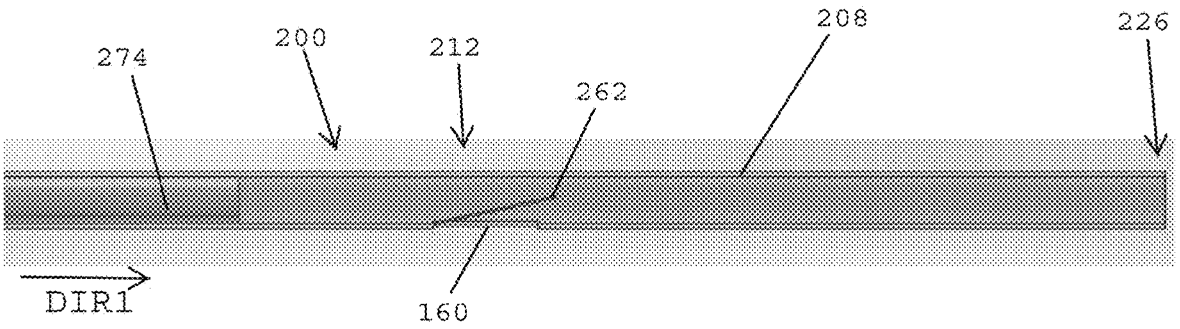
FIG. 25A illustrates a first stage of a method of dispensing a flowable hemostat from a distal end of an elongated dispensing tube of a flowable hemostat dispensing device, the elongated dispensing tube having an air embolism prevention assembly incorporated therein, in accordance with one embodiment of the present application.

Referring to FIG. 25A, in one embodiment, a syringe plunger of a syringe may be depressed for expelling a flowable hemostat material from the syringe and into the elongated conduit of the elongated dispensing tube 208. The flowable hemostat material 274 flows in the distal direction DIR1 toward the distal end 226 of the elongated dispensing tube 208. The flowable hemostat dispensing device 200 preferably includes the air embolism prevention assembly 212 with the flexible flap 262 that is biased into a retracted position so that the flexible flap 262 does not seal the air vent 260 formed in the outer wall of the elongated dispensing tube 208.

Figure 25B:
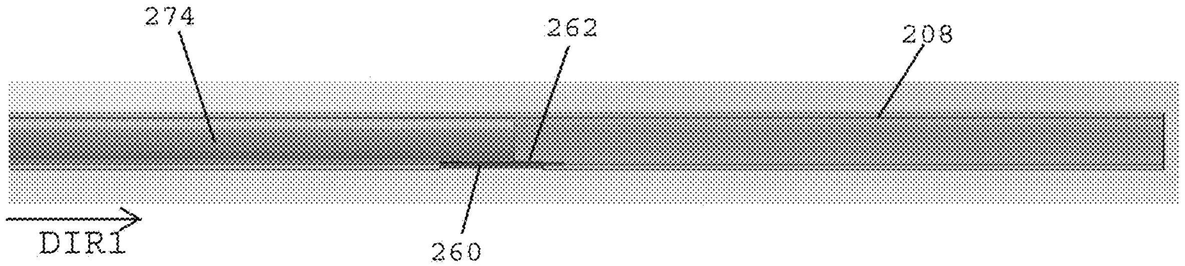
FIG. 25B illustrates a second stage of a method of dispensing a flowable hemostat from a distal end of an elongated dispensing tube of a flowable hemostat dispensing device, in accordance with one embodiment of the present application.

Referring to FIG. 25B, in one embodiment, the flowable hemostat 274 continues to flow in the distal direction DIR1 until the flowable hemostat engages the flexible flap 262 for forcing the flexible flap 262 into the extended position for sealing the air vent opening 260 formed in the outer wall of the elongated dispensing tube 208.

Figure 25C:
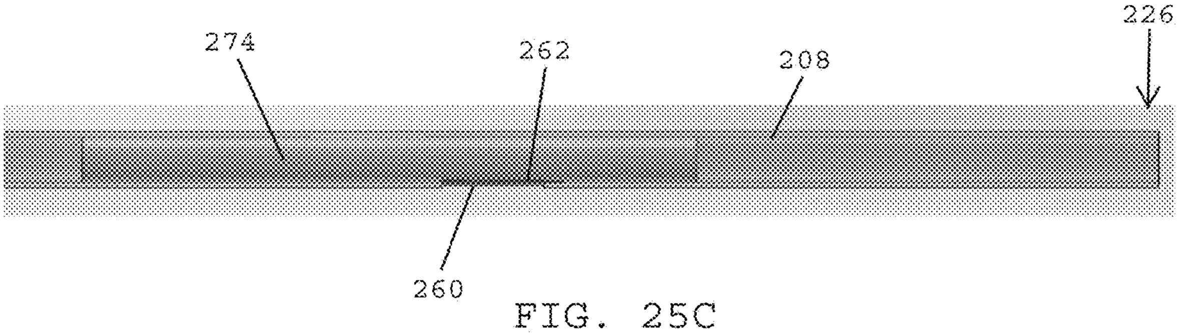
FIG. 25C illustrates a third stage of a method of dispensing a flowable hemostat from a distal end of an elongated dispensing tube of a flowable hemostat dispensing device, in accordance with one embodiment of the present application.
Figure 25D:
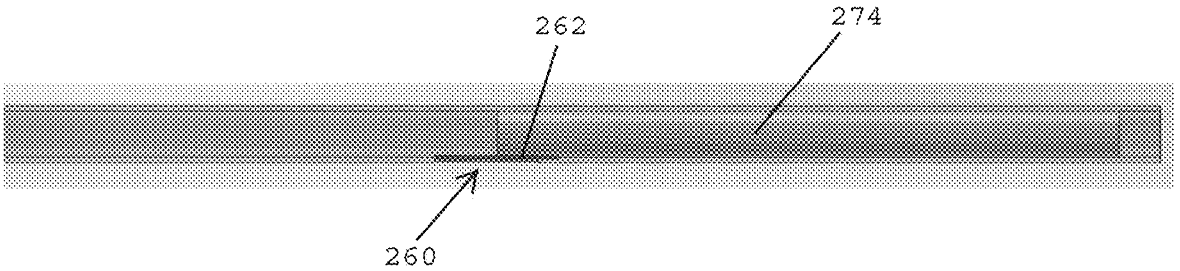
FIG. 25D illustrates a fourth stage of a method of dispensing a flowable hemostat from a distal end of an elongated dispensing tube of a flowable hemostat dispensing device, in accordance with one embodiment of the present application.

Referring to FIGS. 25C and 25D, the flowable hemostat material 274 continues to flow in a distal direction DIR1 toward the distal end 226 of the elongated dispensing tube 208. While the flowable hemostat material 274 remains in contact with the flexible flap 262, the flowable hemostat, having a paste-like or viscous consistency, forces the flexible flap into the extended position for sealing the air vent 260 formed in the outer wall of the elongated dispensing tube 208.

Figure 25E:
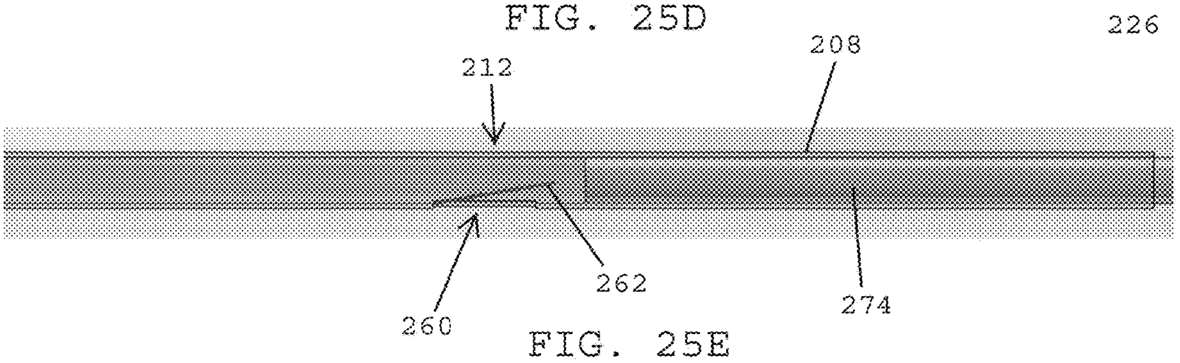
FIG. 25E illustrates a fifth stage of a method of dispensing a flowable hemostat from a distal end of an elongated dispensing tube of a flowable hemostat dispensing device, in accordance with one embodiment of the present application.
Figure 26:
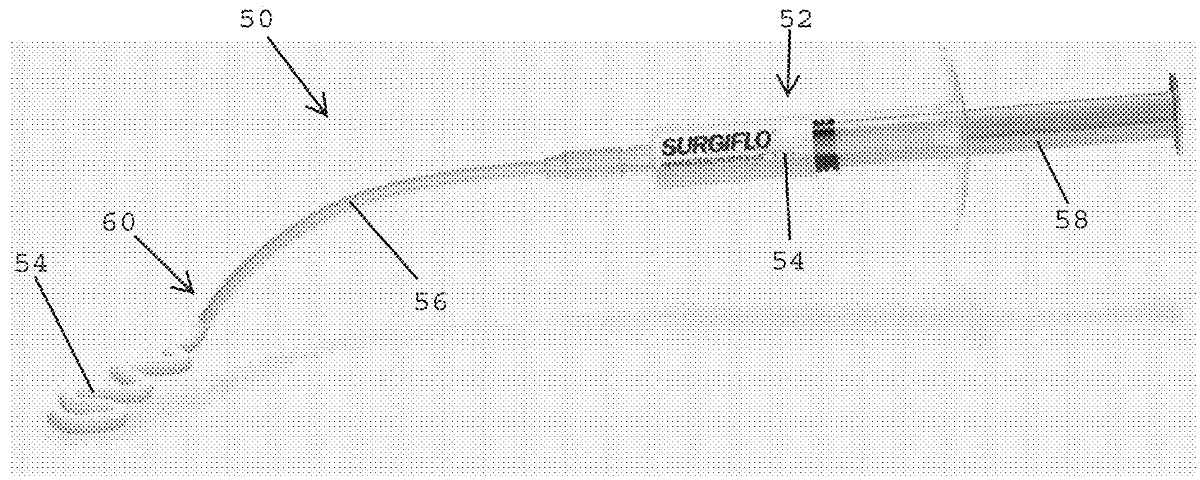
FIG. 26 shows a prior art dispensing device for dispensing a flowable hemostat.
Figure 27A:
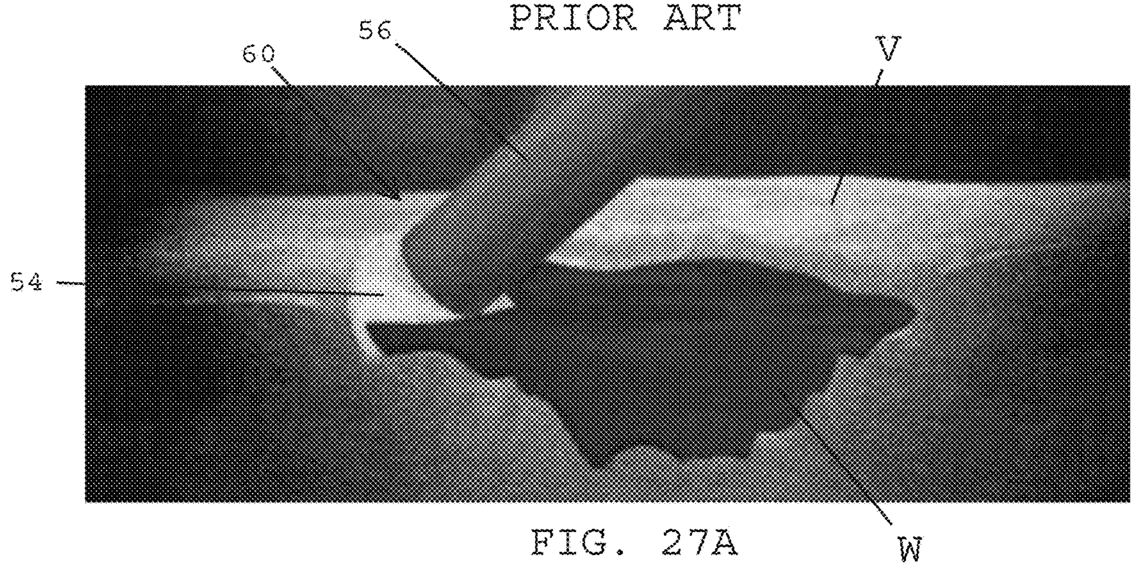
FIG. 27A shows a first stage of a prior art method for dispensing a flowable hemostat to stop bleeding at a surgical site.
Figure 27B:
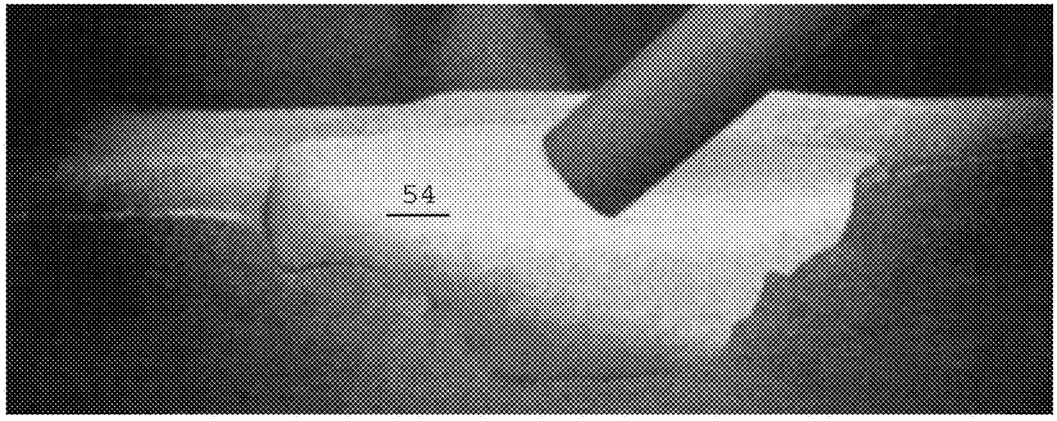
FIG. 27B shows a second stage of a prior art method for dispensing a flowable hemostat to stop bleeding at a surgical site.

Referring to FIG. 25E, in one embodiment, after the flowable hemostat material 274 flows distally beyond the flexible flap 262 of the air embolism prevention assembly 212, the flexible flap 262 is no longer engaged by the residual flowable hemostat material 274 that remains within the distal end of the dispensing tube 208. At this stage, the flexible flap 262 biases back (e.g., springs back) into its normal retracted position for unsealing the air vent opening 260 formed in the outer wall of the elongated dispensing tube 208.

In prior art devices, the residual flowable hemostat 174 that remains inside the distal end of the elongated dispensing tube 208 of the dispensing device is often not used and is deemed to be a sacrificial quantity of flowable hemostat. The residual or sacrificial plug of flowable hemostat is simply not used and is thrown away. This is not cost effective and wastes valuable resources. In some instances, up to 40% of the flowable hemostat that is loaded into a syringe is not used. In some instances, the surgeon may detach the proximal end of the elongated tube 208 from the syringe connector and use a stylus or stick to force the stranded plug of the flowable hemostat from the distal end of the elongated tube 208. Detaching the elongated tube from the syringe connector wastes valuable time during a surgical procedure and forces the surgeon to remove his or her eyes from monitoring the surgical procedure, which could create safety or efficiency issues.

Using the components and methods shown and described above in FIGS. 18-20, the present patent application discloses improved systems, devices, and methods of safely and efficiently expelling and/or pushing the residual flowable hemostat 274 from the distal end of a dispensing device, without requiring the proximal end of the dispensing tube 208 to be detached from a syringe connector and/or a syringe barrel, and without forcing a surgeon to remove his or her eyes from the surgical site.

At the stage shown in FIG. 25E, using the components shown and described above in FIGS. 18-20, air may be forced into the elongated conduit of the elongated dispensing tube 208 for forcing the residual flowable hemostat 274 that remains within the elongated dispensing tube 208 from the distal end 226 of the elongated dispensing tube 208 to push out any residual flowable hemostat material that remains in the elongated dispensing tube. As the air is forced into the elongated dispensing tube 208 and toward the residual flowable hemostat 274, the flexible flap 262 is retracted and the air vent opening 260 is unsealed for enabling the air to be vented to atmosphere through the air vent opening 260 provided in the outer wall of the elongated dispensing tube 208.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A system for dispensing a flowable viscous fluid comprising:

a hollow tube having an outer wall that extends from a proximal end to a distal end of said hollow tube;

at least one air vent formed in said outer wall of said hollow tube adjacent the distal end of said hollow tube; and a valve comprising at least one flexible flap disposed inside said hollow tube, wherein said at least one flexible flap is moveable between a first position for unsealing said at least one vent and a second position for sealing said at least one air vent, and wherein said at least one flexible flap is biased into the first position for unsealing said at least one vent;

wherein the at least one flexible flap is moveable between the first position and the second position to selectively unseal and seal the at least one air vent and wherein the at least one flexible flap is configured to seal the at least one air vent upon a flowable hemostatic material flowing in the tube past the valve.

2. The dispensing system as claimed in claim 1, wherein said at least one air vent comprises two or more air vents formed in said outer wall of said hollow tube, and wherein said at least one flexible flap comprises two or more flexible flaps, each said flexible flap being configured for sealing and unsealing said air vent associated therewith.

3. The dispensing system as claimed in claim 1, wherein said at least one air vent comprises four air vents that are formed in said outer wall of said hollow tube and that are evenly spaced from one another adjacent the distal end of said hollow tube.

4. The dispensing system as claimed in claim 3, wherein said at least one flexible flap comprises:

a first flexible flap that is configured for sealing and unsealing a first air vent of said four air vents;

a second flexible flap that is configured for sealing and unsealing a second air vent of said four air vents;

a third flexible flap that is configured for sealing and unsealing a third air vent of said four air vents; and a fourth flexible flap that is configured for sealing and unsealing a fourth air vent of said four air vents.

5. The dispensing system as claimed in claim 4, wherein said valve comprises a valve ring having a proximal edge and a distal edge, wherein said four flexible flaps have proximal ends that are hingedly connected with said distal edge of said valve ring.

6. The dispensing system as claimed in claim 5, wherein said valve ring and said four flexible flaps are disposed inside said hollow tube so that said four flexible flaps are distal to said valve ring and so that said four flexible flaps are aligned with said four air vents, respectively.

7. The dispensing system as claimed in claim 6, wherein said four flexible flaps are evenly spaced from one another around a perimeter of said valve ring.

8. The dispensing system as claimed in claim 6, further comprising at least one stop disposed inside said hollow tube and projecting inwardly from an inner surface of said outer wall of said hollow tube, wherein said distal edge of said valve ring is in contact with said at least one stop for securing said valve in place inside said hollow tube.

9. The dispensing system as claimed in claim 1, further comprising:

a syringe including a syringe barrel and a syringe plunger that is disposed inside said syringe barrel;

a syringe connector having a proximal end coupled with a distal end of said syringe barrel and a distal end coupled with said proximal end of said hollow tube, wherein said syringe connector has a fluid conduit that extends from said proximal end to said distal end of said syringe connector to define a fluid flow path between said syringe barrel and said hollow tube.

10. The dispensing system as claimed in claim 9, further comprising a one-way fluid valve disposed within said fluid flow path of said syringe connector that permits fluid to flow in a distal direction while preventing backflow of said fluid in a proximal direction.

11. The dispensing system as claimed in claim 10, further comprising:

an air inlet formed in said syringe connector that intersects with said fluid flow path;

a one-way air valve disposed in said air inlet that allows air to flow inwardly from said air inlet to said fluid flow path while preventing said air from flowing outwardly from said fluid flow path to said air inlet.

12. The dispensing system as claimed in claim 11, further comprising:

a second air inlet formed in said syringe connector that intersects with said fluid flow path;

a second one-way air valve disposed in said second air inlet that allows air to flow inwardly from said second air inlet to said fluid flow path while preventing said air from flowing outwardly from said fluid flow path to said air inlet.

13. The dispensing system as claimed in claim 12, wherein said first and second air inlets have inner ends that intersect with said fluid flow path at a section of said fluid flow path that is located between said one-way fluid valve and said proximal end of said syringe connector.

14. The dispensing system as claimed in claim 9, further comprising a flowable viscous fluid disposed within said syringe barrel, wherein depressing said syringe plunger toward said distal end of said syringe barrel expels said flowable viscous fluid from said syringe barrel and forces said flowable viscous fluid through said fluid flow path of said syringe connector and into said proximal end of said elongated hollow tube.

15. A system for dispensing a flowable viscous fluid comprising:

an elongated hollow tube having a proximal end, a distal end, and an outer wall that extends from the proximal end to the distal end of said elongated hollow tube;

at least one an air vent formed in said outer wall adjacent the distal end of said elongated hollow tube;

a valve comprising at least one flexible flap disposed inside said elongated hollow tube, said at least one flexible flap being moveable between an extended position for sealing said at least one air vent and a retracted position for unsealing said at least one air vent, wherein said at least one flexible flap is normally biased into the retracted position for unsealing said at least one air vent;

a syringe including a syringe barrel and a syringe plunger that is disposed inside said syringe barrel;

a syringe connector having a proximal end coupled with a distal end of said syringe barrel and a distal end coupled with said proximal end of said elongated hollow tube, wherein said syringe connector has a fluid conduit that extends from said proximal end to said distal end of said syringe connector that defines a fluid flow path that extends between said syringe barrel and said elongated hollow tube; and a flowable viscous fluid disposed within said syringe barrel, wherein said syringe plunger is adapted for being depressed toward said distal end of said syringe barrel for expelling said flowable viscous fluid from said syringe barrel and forcing said flowable viscous fluid through said fluid flow path of said syringe connector and into said proximal end of said elongated hollow tub, wherein said at least one air vent comprises four air vents that are formed in said outer wall of said hollow tube and that are evenly spaced from one another adjacent the distal end of said hollow tube, wherein said at least one flexible flap comprises a first flexible flap that is configured for sealing and unsealing a first air vent of said four air vents, a second flexible flap that is configured for sealing and unsealing a second air vent of said four air vents, a third flexible flap that is configured for sealing and unsealing a third air vent of said four air vents, and a fourth flexible flap that is configured for sealing and unsealing a fourth air vent of said four air vents, and wherein said valve comprises a valve ring having a proximal edge and a distal edge, wherein said four flexible flaps have proximal ends that are hingedly connected with said distal edge of said valve ring, wherein said valve ring and said four flexible flaps are disposed inside said elongated hollow tube so that said four flexible flaps are distal to said valve ring and so that said four flexible flaps are aligned with said four air vents, respectively, and wherein said four flexible flaps are evenly spaced from one another around a perimeter of said valve ring.

16. The dispensing system as claimed in claim 15, further comprising:

a one-way fluid valve disposed within said fluid flow path of said syringe connector that permits fluid to flow in a distal direction while preventing backflow of said fluid in a proximal direction;

an air inlet formed in said syringe connector that intersects with said fluid flow path; and a one-way air valve disposed in said air inlet that allows air to flow inwardly from said air inlet to said fluid flow path while preventing said air from flowing outwardly from said fluid flow path to said air inlet, wherein said air inlet has an inner end that intersect with said fluid flow path at a section of said fluid flow path that is located between said one-way fluid valve and said proximal end of said syringe connector.

17. A method of dispensing a flowable viscous fluid comprising:

obtaining a hollow tube having an outer wall with at least one air vent formed in said outer wall at a location that is adjacent a distal end of said hollow tube, said hollow tube including a valve having at least one flexible flap disposed inside said hollow tube that is normally biased in an open position for unsealing said at least one air vent;

forcing a mass of a flowable viscous fluid into said hollow tube and toward a distal end of said hollow tube until said mass of said flowable viscous material engages said at least one flexible flap for forcing said at least one flexible flap to move into a closed position for sealing said at least one air vent; and after said forcing said mass step, directing air into a proximal end of said hollow tube whereupon said air forces said mass of said flowable viscous fluid to move in a distal direction beyond a distal end of said at least one flexible flap so that said air engages said at least one flexible flap whereupon said at least one flexible flap moves back to said biased open position for unsealing said at least one air vent, wherein said at least one air vent comprises four air vents that are formed in said outer wall of said hollow tube and that are evenly spaced from one another adjacent the distal end of said hollow tube, wherein said at least one flexible flap comprises a first flexible flap that is configured for sealing and unsealing a first air vent of said four air vents, a second flexible flap that is configured for sealing and unsealing a second air vent of said four air vents, a third flexible flap that is configured for sealing and unsealing a third air vent of said four air vents, and a fourth flexible flap that is configured for sealing and unsealing a fourth air vent of said four air vents, and wherein said valve comprises a valve ring having a proximal edge and a distal edge, wherein said four flexible flaps have proximal ends that are hingedly connected with said distal edge of said valve ring, wherein said valve ring and said four flexible flaps are disposed inside said elongated hollow tube so that said four flexible flaps are distal to said valve ring and so that said four flexible flaps are aligned with said four air vents, respectively, and wherein said four flexible flaps are evenly spaced from one another around a perimeter of said valve ring.

* * * * *